United States Patent
Anastasov et al.

(10) Patent No.: US 10,072,273 B2
(45) Date of Patent: Sep. 11, 2018

(54) PSEUDOTYPED LENTIVIRAL VECTORS

(71) Applicants: SIRION BIOTECH GMBH, Martinsried (DE); Helmholtz Zentrum München—Deutsches Forschungszentrum für Gesundheit und Umwelt (GmbH), Neuherberg (DE)

(72) Inventors: Nataša Anastasov, München (DE); Ines Höfig, München (DE); Christian Thirion, Martinsried (DE)

(73) Assignees: Helmholtz Zentrum München—Deutsches Forschungszentrum Für Gesundheit Und Umwelt (GMBH), Neuherberg (DE); Sirion Biotech GmbH, Martinsried (DE)

( * ) Notice: Subject to any disclaimer, the term of this patent is extended or adjusted under 35 U.S.C. 154(b) by 0 days.

(21) Appl. No.: 15/110,924

(22) PCT Filed: Jan. 9, 2015

(86) PCT No.: PCT/EP2015/050337
§ 371 (c)(1),
(2) Date: Jul. 11, 2016

(87) PCT Pub. No.: WO2015/104376
PCT Pub. Date: Jul. 16, 2015

(65) Prior Publication Data
US 2016/0333374 A1 Nov. 17, 2016

(30) Foreign Application Priority Data
Jan. 10, 2014 (EP) .................... 14150846

(51) Int. Cl.
*C12N 15/86* (2006.01)
*C12N 7/00* (2006.01)
*C07K 14/005* (2006.01)
*C07K 16/28* (2006.01)

(52) U.S. Cl.
CPC ........... *C12N 15/86* (2013.01); *C07K 14/005* (2013.01); *C07K 16/2863* (2013.01); *C07K 16/2878* (2013.01); *C12N 7/00* (2013.01); *C07K 2317/622* (2013.01); *C07K 2319/02* (2013.01); *C07K 2319/33* (2013.01); *C07K 2319/74* (2013.01); *C12N 2740/15042* (2013.01); *C12N 2740/15043* (2013.01); *C12N 2740/15045* (2013.01); *C12N 2740/15052* (2013.01); *C12N 2740/16045* (2013.01); *C12N 2760/20222* (2013.01); *C12N 2810/6081* (2013.01); *C12N 2810/859* (2013.01)

(58) Field of Classification Search
None
See application file for complete search history.

(56) References Cited

FOREIGN PATENT DOCUMENTS

| EP | 2615176 A1 | 7/2013 |
|---|---|---|
| WO | 2013/127964 A1 | 9/2013 |

OTHER PUBLICATIONS

Ammayappan et al., Journal of Virology, 2013, 87(24):13543-13555.*
Waehler et al., "Engineering targeted viral vectors for gene therapy," Nature Reviews, Genetics, vol. 8, Aug. 2007, pp. 573-587.
Guibinga et al., "Ligand-Modified Vesicular Stomatitis Virus Glycoprotein Displays a Temperature-Sensitive Intracellular Trafficking and Virus Assembly Phenotype," Molecular Therapy, vol. 9, No. 1, Jan. 2004, pp. 76-84.
Kameyama et al., "Antibody-dependent gene transduction using gammaretroviral and lentiviral vectors pseudotyped with chimeric vesicular stomatitis virus glycoprotein," Journal of Virological Methods 153 (2008) pp. 49-54.
Padmashali et al., "Engineering fibrinogen-binding VSV-G envelope for spatially- and cell-controlled lentivirus delivery trough fibrin hydrogels," Biomaterials 32 (2011) pp. 3330-3339.
Dreja et al., "The effects of N-terminal insertion into VSV-G of an scFv peptide," Virology Journal, 2006, 3:69, pp. 1-8.
Finkelshtein et al., "LDL receptor and its family members serve as the cellular receptors for vesicular stomatitis virus," PNAS, Apr. 30, 2013, vol. 110, No. 18, pp. 7306-7311.
Burns et al., "Vesicular stomatitis virus G glycoprotein pseudotyped retroviral vectors: Concentration to very high titer and efficient gene transfer into mammalian and nonmammalian cells," Proc. Natl. Acad. Sci USA, vol. 90, Sep. 1993, pp. 8033-8037.

(Continued)

*Primary Examiner* — Nicole Kinsey White
(74) *Attorney, Agent, or Firm* — Briggs and Morgan, P.A.; Audrey J. Babcock

(57) ABSTRACT

The present invention relates to a nucleic acid molecule comprising or consisting of a nucleic acid sequence encoding the vesicular stomatitis virus envelope glycoprotein (VSV-G) linked to a (poly)peptide comprising or consisting of a cell membrane-binding domain, said nucleic acid sequence comprising in 5' to 3' direction (a) a first sequence segment encoding an endoplasmic reticulum (ER) signal sequence; (b) a second sequence segment encoding said (poly)peptide comprising or consisting of a cell membrane-binding domain; (c) a third sequence segment encoding a linker; and (d) a fourth sequence segment encoding said VSV-G. Further, the invention relates to a vector comprising the nucleic acid molecule of the invention, a host cell comprising said vector or nucleic acid molecule, the polypeptide encoded by said nucleic acid molecule and a method of producing the polypeptide encoded by said nucleic acid molecule. In addition, the invention relates to a pseudotyped lentiviral vector particle, a method of transducing a cell as well as a kit comprising various combinations of the nucleic acid molecule, vectors, polypeptides and host cells of the invention.

Figure 1:
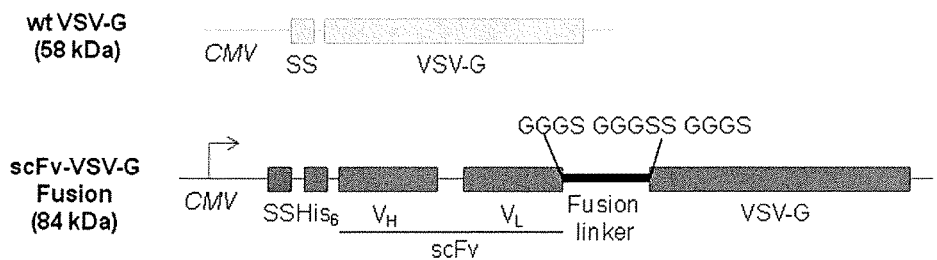

18 Claims, 7 Drawing Sheets
Specification includes a Sequence Listing.

(56) References Cited

OTHER PUBLICATIONS

Li et al., "Mutational Analysis of the Vesicular Stomatitis Virus Glycoprotein G for Membrane Fusion Domains," Journal of Virology, vol. 67, No. 7, Jul. 1993, pp. 4070-4077.
Ammayappan et al., "Characteristics of Oncolytic Vesicular Stomatitis Virus Displaying Tumor-Targeting Ligands," Journal of Virology, vol. 87, No. 24, pp. 13543-13555, Oct. 2, 2013.
Anliker, et al., "Specific gene transfer to neurons, endothelial cells and hematopoietic progenitors with lentiviral vectors," Nature Methods, vol. 7, No. 11, pp. 929-937, Nov. 2010.
Froelich, et al., "Lentiviral Vectors for Immune Cells Targeting," Immunopharmacol Immunotoxicol. 32(2): 208-218, Jun. 2010.
Hofig et al., "Poloxamer synperonic F108 improves cellular transduction with lentiviral vectors," J. Gene Med 2012; 14:549-560.
Luong, et al., "Construction of Lentiviruses Pseudotyped with Sindbis E2-Single Chain Andibody (SCA) Fusions or Membrane-Anchored SCAs for Targeted Therapies in Lymphoma," Blood (ASH Annual Meeting Abstracts) 2009 114: Abstract 3571.
Yang, et al., "Targeting lentiviral vectors to specific cell types in vivo," PNAS, vol. 103, No. 31, pp. 11479-11484, Aug. 1, 2006.
International Search Report of PCT/EP2015/050337 dated Mar. 18, 2015.

\* cited by examiner

SEQUENCE LISTING

<160> NUMBER OF SEQ ID NOS: 14

<210> SEQ ID NO 1
<211> LENGTH: 48
<212> TYPE: DNA
<213> ORGANISM: Artificial Sequence

```
<220> FEATURE:
<221> NAME/KEY: source
<222> LOCATION: 1..48
<223> OTHER INFORMATION: /mol_type="unassigned DNA"
      /note="Endoplasmic reticulum (ER) signal sequence of VSV-G"
      /organism="Artificial Sequence"

<400> SEQUENCE: 1
atgaagtgcc ttttgtactt agccttttta ttcattgggg tgaattgc             48

<210> SEQ ID NO 2
<211> LENGTH: 16
<212> TYPE: PRT
<213> ORGANISM: Artificial Sequence
<220> FEATURE:
<223> OTHER INFORMATION: Endoplasmic reticulum (ER) signal sequence of
      VSV-G

<400> SEQUENCE: 2

Met Lys Cys Leu Leu Tyr Leu Ala Phe Leu Phe Ile Gly Val Asn Cys
1               5                   10                  15

<210> SEQ ID NO 3
<211> LENGTH: 39
<212> TYPE: DNA
<213> ORGANISM: Artificial Sequence
<220> FEATURE:
<221> NAME/KEY: source
<222> LOCATION: 1..39
<223> OTHER INFORMATION: /mol_type="unassigned DNA"
      /note="Linker between scFv and VSV-G"
      /organism="Artificial Sequence"

<400> SEQUENCE: 3
ggaggcggtt caggaggtgg ctcgagcgga ggcggttca                       39

<210> SEQ ID NO 4
<211> LENGTH: 13
<212> TYPE: PRT
<213> ORGANISM: Artificial Sequence
<220> FEATURE:
<223> OTHER INFORMATION: Linker between scFv and VSV-G

<400> SEQUENCE: 4

Gly Gly Gly Ser Gly Gly Gly Ser Ser Gly Gly Gly Ser
1               5                   10

<210> SEQ ID NO 5
<211> LENGTH: 1488
<212> TYPE: DNA
<213> ORGANISM: Artificial Sequence
<220> FEATURE:
<221> NAME/KEY: source
<222> LOCATION: 1..1488
<223> OTHER INFORMATION: /mol_type="unassigned DNA"
      /note="VSV-G without signal sequence"
      /organism="Artificial Sequence"

<400> SEQUENCE: 5
aagttcacca tagtttttcc acacaaccaa aaaggaaact ggaaaaatgt tccttctaat    60
taccattatt gcccgtcaag ctcagattta aattggcata atgacttaat aggcacagcc   120
atacaagtca aaatgcccaa gagtcacaag gctattcaag cagacggttg gatgtgtcat   180
gcttccaaat gggtcactac ttgtgatttc cgctggtatg gaccgaagta tataacacag   240
tccatccgat cctcactcc atctgtagaa caatgcaagg aaagcattga acaaacgaaa    300
caaggaactt ggctgaatcc aggcttccct cctcaaagtt gtggatatgc aactgtgacg   360
```

```
gatgccgaag cagtgattgt ccaggtgact cctcaccatg tgctggttga tgaatacaca    420
ggagaatggg ttgattcaca gttcatcaac ggaaaatgca gcaattacat atgcccact     480
gtccataact ctacaacctg gcattctgac tataaggtca aagggctatg tgattctaac    540
ctcatttcca tggacatcac cttcttctca gaggacggag agctatcatc cctgggaaag    600
gagggcacag ggttcagaag taactacttt gcttatgaaa ctggaggcaa ggcctgcaaa    660
atgcaatact gcaagcattg gggagtcaga ctcccatcag gtgtctggtt cgagatggct    720
gataaggatc tctttgctgc agccagattc cctgaatgcc cagaagggtc aagtatctct    780
gctccatctc agacctcagt ggatgtaagt ctaattcagg acgttgagag gatcttggat    840
tattccctct gccaagaaac ctggagcaaa atcagagcgg tcttccaat ctctccagtg     900
gatctcagct atcttgctcc taaaaaccca ggaaccggtc ctgctttcac cataatcaat    960
ggtaccctaa atactttga ccagatac atcagagtcg atattgctgc tccaatcctc      1020
tcaagaatgg tcggaatgat cagtggaact accacagaaa gggaactgtg ggatgactgg    1080
gcaccatatg aagacgtgga aattggaccc aatggagttc tgaggaccag ttcaggatat    1140
aagtttcctt tatacatgat tggacatggt atgttggact ccgatcttca tcttagctca    1200
aaggctcagg tgttcgaaca tcctcacatt caagacgctg cttcgcaact tcctgatgat    1260
gagagtttat tttttggtga tactgggcta tccaaaaatc caatcgagct tgtagaaggt    1320
tggttcagta gttggaaaag ctctattgcc tcttttttct ttatcatagg gttaatcatt    1380
ggactattct tggttctccg agttggtatc catctttgca ttaaattaaa gcacaccaag    1440
aaaagacaga tttatacaga catagagatg aaccgacttg gaaagtaa                1488
```

<210> SEQ ID NO 6
<211> LENGTH: 495
<212> TYPE: PRT
<213> ORGANISM: Artificial Sequence
<220> FEATURE:
<223> OTHER INFORMATION: VSV-G without signal sequence

<400> SEQUENCE: 6

```
Lys Phe Thr Ile Val Phe Pro His Asn Gln Lys Gly Asn Trp Lys Asn
1               5                   10                  15

Val Pro Ser Asn Tyr His Tyr Cys Pro Ser Ser Ser Asp Leu Asn Trp
            20                  25                  30

His Asn Asp Leu Ile Gly Thr Ala Ile Gln Val Lys Met Pro Lys Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
65                  70                  75                  80

Ser Ile Arg Ser Phe Thr Pro Ser Val Glu Gln Cys Lys Glu Ser Ile
                85                  90                  95

Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160
```

Val His Asn Ser Thr Thr Trp His Ser Asp Tyr Lys Val Lys Gly Leu
            165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
            195                 200                 205

Tyr Phe Ala Tyr Glu Thr Gly Gly Lys Ala Cys Lys Met Gln Tyr Cys
            210                 215                 220

Lys His Trp Gly Val Arg Leu Pro Ser Gly Val Trp Phe Glu Met Ala
225                 230                 235                 240

Asp Lys Asp Leu Phe Ala Ala Arg Phe Pro Glu Cys Pro Glu Gly
            245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
            275                 280                 285

Ser Lys Ile Arg Ala Gly Leu Pro Ile Ser Pro Val Asp Leu Ser Tyr
            290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
            325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
            355                 360                 365

Gly Pro Asn Gly Val Leu Arg Thr Ser Ser Gly Tyr Lys Phe Pro Leu
            370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
            405                 410                 415

Leu Pro Asp Asp Glu Ser Leu Phe Phe Gly Asp Thr Gly Leu Ser Lys
            420                 425                 430

Asn Pro Ile Glu Leu Val Glu Gly Trp Phe Ser Ser Trp Lys Ser Ser
            435                 440                 445

Ile Ala Ser Phe Phe Phe Ile Ile Gly Leu Ile Ile Gly Leu Phe Leu
450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
            485                 490                 495

<210> SEQ ID NO 7
<211> LENGTH: 2325
<212> TYPE: DNA
<213> ORGANISM: Artificial Sequence
<220> FEATURE:
<221> NAME/KEY: source
<222> LOCATION: 1..2325
<223> OTHER INFORMATION: /mol_type="unassigned DNA"
     /note="scFvCD30-VSV-G (Signal sequence of VSV-G - His-Tag -
     scFvCD30 - Linker - VSV-G)"
     /organism="Artificial Sequence"

```
<400> SEQUENCE: 7
atgaagtgcc ttttgtactt agccttttta ttcattgggg tcaattgcca tcatcatcat    60
catcatgccc aggtcaagct gcaggagtca gggactgaac tggcaaagcc tggggccgca   120
gtgaagatgt cctgcaaggc ttctggctac acctttactg actactggat gcactgggtt   180
aaacagaggc ctggacaggg tctggaatgg attggataca ttaatcctaa cactgcttat   240
actgactaca atcagaaatt caaggacaag gccacattga ctgcagacaa atcctccagc   300
acagcctaca tgcaactgcg cagcctgacc tctgaggatt ctgcagtcta ttactgtgca   360
aaaaagacaa ctcagactac gtgggggttt ccttttgggg ccaagggac cacggtcacc   420
gtctcctcag gtggaggcgg ttcaggcgga ggtggctctg gcggtggcgg atcggacatt   480
gtgctgaccc agtctccaaa atccatggcc atgtcagtcg gagagagggt caccttgagc   540
tgcaaggcca gtgagaatgt ggattctttt gtttcctggt atcaacagaa accaggccag   600
tctcctaaac tgctgatata cgggcctcc aaccggtaca ctgggtccc cgatcgcttc   660
gcaggcagtg gatctggaag agatttcact ctgaccatca gcagtgtgca ggctgaagac   720
cttgcagatt atcactgtgg acagaattac aggtatccgc tcacgttcgg tgctggcacc   780
aagctggaaa tcaaacgggg aggcggttca ggaggtggct cgagcggagg cggttcaaag   840
ttcaccatag ttttccaca caaccaaaaa ggaaactgga aaatgttcc ttctaattac   900
cattattgcc cgtcaagctc agatttaaat tggcataatg acttaatagg cacagccata   960
caagtcaaaa tgcccaagag tcacaaggct attcaagcag acggttggat gtgtcatgct  1020
tccaaatggg tcactacttg tgatttccgc tggtatggac cgaagtatat aacacagtcc  1080
atccgatcct tcactccatc tgtagaacaa tgcaaggaaa gcattgaaca acgaaacaa  1140
ggaacttggc tgaatccagg cttccctcct caaagttgtg gatatgcaac tgtgacggat  1200
gccgaagcag tgattgtcca ggtgactcct caccatgtgc tggttgatga atacacagga  1260
gaatggggttg attcacagtt catcaacgga aaatgcagca attacatatg ccccactgtc  1320
cataactcta caacctggca ttctgactat aaggtcaaag gctatgtga ttctaacctc  1380
atttccatgg acatcacctt cttctcagag gacgagagc tatcatccct gggaaaggag  1440
ggcacagggt tcagaagtaa ctactttgct tatgaaactg gaggcaaggc ctgcaaaatg  1500
caatactgca gcattggggg agtcagactc ccatcaggtg tctggttcga gatggctgat  1560
aaggatctct ttgctgcagc cagattccct gaatgcccag aagggtcaag tatctctgct  1620
ccatctcaga cctcagtgga tgtaagtcta attcaggacg ttgagaggat cttggattat  1680
tccctctgcc aagaaacctg gagcaaaatc agagcgggtc ttccaatctc tccagtggat  1740
ctcagctatc ttgctcctaa aaacccagga accggtcctg ctttcaccat aatcaatggt  1800
accctaaaat actttgagac cagatacatc agagtcgata ttgctgctcc aatcctctca  1860
agaatggtcg gaatgatcag tggaactacc acagaaaggg aactgtggga tgactgggca  1920
ccatatgaag acgtggaaat tggacccaat ggagttctga ggaccagttc aggatataag  1980
tttcctttat acatgattgg acatggtatg ttggactccg atcttcatct tagctcaaag  2040
gctcaggtgt cgaacatcc tcacattcaa gacgctgctt cgcaacttcc tgatgatgag  2100
agtttatttt ttggtgatac tgggctatcc aaaaatccaa tcgagcttgt agaaggttgg  2160
ttcagtagtt ggaaaagctc tattgcctct ttttctttta tcatagggtt aatcattgga  2220
ctattcttgg ttctccgagt tggtatccat cttttgcatta aattaaagca caccaagaaa  2280
agacagattt atacagacat agagatgaac cgacttggaa agtaa              2325
```

```
<210> SEQ ID NO 8
<211> LENGTH: 774
<212> TYPE: PRT
<213> ORGANISM: Artificial Sequence
<220> FEATURE:
<223> OTHER INFORMATION: scFvCD30-VSV-G (Signal sequence of VSV-G-His-
      Tag-scFvCD30-Linker-VSV-G)

<400> SEQUENCE: 8

Met Lys Cys Leu Leu Tyr Leu Ala Phe Leu Phe Ile Gly Val Asn Cys
1               5                   10                  15

His His His His His His Ala Gln Val Lys Leu Gln Glu Ser Gly Thr
            20                  25                  30

Glu Leu Ala Lys Pro Gly Ala Ala Val Lys Met Ser Cys Lys Ala Ser
        35                  40                  45

Gly Tyr Thr Phe Thr Asp Tyr Trp Met His Trp Val Lys Gln Arg Pro
    50                  55                  60

Gly Gln Gly Leu Glu Trp Ile Gly Tyr Ile Asn Pro Asn Thr Ala Tyr
65                  70                  75                  80

Thr Asp Tyr Asn Gln Lys Phe Lys Asp Lys Ala Thr Leu Thr Ala Asp
                85                  90                  95

Lys Ser Ser Ser Thr Ala Tyr Met Gln Leu Arg Ser Leu Thr Ser Glu
            100                 105                 110

Asp Ser Ala Val Tyr Tyr Cys Ala Lys Lys Thr Thr Gln Thr Thr Trp
        115                 120                 125

Gly Phe Pro Phe Trp Gly Gln Gly Thr Thr Val Thr Val Ser Ser Gly
    130                 135                 140

Gly Gly Gly Ser Gly Gly Gly Gly Ser Gly Gly Gly Gly Ser Asp Ile
145                 150                 155                 160

Val Leu Thr Gln Ser Pro Lys Ser Met Ala Met Ser Val Gly Glu Arg
                165                 170                 175

Val Thr Leu Ser Cys Lys Ala Ser Glu Asn Val Asp Ser Phe Val Ser
            180                 185                 190

Trp Tyr Gln Gln Lys Pro Gly Gln Ser Pro Lys Leu Leu Ile Tyr Gly
        195                 200                 205

Ala Ser Asn Arg Tyr Thr Gly Val Pro Asp Arg Phe Ala Gly Ser Gly
    210                 215                 220

Ser Gly Arg Asp Phe Thr Leu Thr Ile Ser Ser Val Gln Ala Glu Asp
225                 230                 235                 240

Leu Ala Asp Tyr His Cys Gly Gln Asn Tyr Arg Tyr Pro Leu Thr Phe
                245                 250                 255

Gly Ala Gly Thr Lys Leu Glu Ile Lys Arg Gly Gly Gly Ser Gly Gly
            260                 265                 270

Gly Ser Ser Gly Gly Gly Ser Lys Phe Thr Ile Val Phe Pro His Asn
        275                 280                 285

Gln Lys Gly Asn Trp Lys Asn Val Pro Ser Asn Tyr His Tyr Cys Pro
    290                 295                 300

Ser Ser Ser Asp Leu Asn Trp His Asn Asp Leu Ile Gly Thr Ala Ile
305                 310                 315                 320

Gln Val Lys Met Pro Lys Ser His Lys Ala Ile Gln Ala Asp Gly Trp
                325                 330                 335

Met Cys His Ala Ser Lys Trp Val Thr Thr Cys Asp Phe Arg Trp Tyr
            340                 345                 350

Gly Pro Lys Tyr Ile Thr Gln Ser Ile Arg Ser Phe Thr Pro Ser Val
        355                 360                 365
```

```
Glu Gln Cys Lys Glu Ser Ile Glu Gln Thr Lys Gln Gly Thr Trp Leu
370                 375                 380
Asn Pro Gly Phe Pro Pro Gln Ser Cys Gly Tyr Ala Thr Val Thr Asp
385                 390                 395                 400
Ala Glu Ala Val Ile Val Gln Val Thr Pro His His Val Leu Val Asp
                405                 410                 415
Glu Tyr Thr Gly Glu Trp Val Asp Ser Gln Phe Ile Asn Gly Lys Cys
                420                 425                 430
Ser Asn Tyr Ile Cys Pro Thr Val His Asn Ser Thr Thr Trp His Ser
            435                 440                 445
Asp Tyr Lys Val Lys Gly Leu Cys Asp Ser Asn Leu Ile Ser Met Asp
450                 455                 460
Ile Thr Phe Phe Ser Glu Asp Gly Glu Leu Ser Ser Leu Gly Lys Glu
465                 470                 475                 480
Gly Thr Gly Phe Arg Ser Asn Tyr Phe Ala Tyr Glu Thr Gly Gly Lys
                485                 490                 495
Ala Cys Lys Met Gln Tyr Cys Lys His Trp Gly Val Arg Leu Pro Ser
                500                 505                 510
Gly Val Trp Phe Glu Met Ala Asp Lys Asp Leu Phe Ala Ala Ala Arg
            515                 520                 525
Phe Pro Glu Cys Pro Glu Gly Ser Ser Ile Ser Ala Pro Ser Gln Thr
530                 535                 540
Ser Val Asp Val Ser Leu Ile Gln Asp Val Glu Arg Ile Leu Asp Tyr
545                 550                 555                 560
Ser Leu Cys Gln Glu Thr Trp Ser Lys Ile Arg Ala Gly Leu Pro Ile
                565                 570                 575
Ser Pro Val Asp Leu Ser Tyr Leu Ala Pro Lys Asn Pro Gly Thr Gly
                580                 585                 590
Pro Ala Phe Thr Ile Ile Asn Gly Thr Leu Lys Tyr Phe Glu Thr Arg
            595                 600                 605
Tyr Ile Arg Val Asp Ile Ala Ala Pro Ile Leu Ser Arg Met Val Gly
610                 615                 620
Met Ile Ser Gly Thr Thr Thr Glu Arg Glu Leu Trp Asp Asp Trp Ala
625                 630                 635                 640
Pro Tyr Glu Asp Val Glu Ile Gly Pro Asn Gly Val Leu Arg Thr Ser
                645                 650                 655
Ser Gly Tyr Lys Phe Pro Leu Tyr Met Ile Gly His Gly Met Leu Asp
                660                 665                 670
Ser Asp Leu His Leu Ser Ser Lys Ala Gln Val Phe Glu His Pro His
            675                 680                 685
Ile Gln Asp Ala Ala Ser Gln Leu Pro Asp Asp Glu Ser Leu Phe Phe
690                 695                 700
Gly Asp Thr Gly Leu Ser Lys Asn Pro Ile Glu Leu Val Glu Gly Trp
705                 710                 715                 720
Phe Ser Ser Trp Lys Ser Ser Ile Ala Ser Phe Phe Ile Ile Gly
                725                 730                 735
Leu Ile Ile Gly Leu Phe Leu Val Leu Arg Val Gly Ile His Leu Cys
                740                 745                 750
Ile Lys Leu Lys His Thr Lys Lys Arg Gln Ile Tyr Thr Asp Ile Glu
            755                 760                 765
Met Asn Arg Leu Gly Lys
            770
```

-continued

```
<210> SEQ ID NO 9
<211> LENGTH: 2344
<212> TYPE: DNA
<213> ORGANISM: Artificial Sequence
<220> FEATURE:
<221> NAME/KEY: source
<222> LOCATION: 1..2344
<223> OTHER INFORMATION: /mol_type="unassigned DNA"
      /note="scFvEGFR-VSV-G (Signal sequence of VSV-G - His-Tag -
      scFvEGFR - Linker - VSV-G)"
      /organism="Artificial Sequence"

<400> SEQUENCE: 9
atgaagtgcc ttttgtactt agccttttta ttcattgggg tcaattgcca tcatcatcat      60
catcatgccg aggtgcaact gcagcagtct ggggctgaac tggtgaagcc tggggcttca     120
gtgaagttgt cctgcaaggc ttccggctac accttcacca gccactggat gcactgggtg     180
aagcagaggg ctggacaagg ccttgagtgg atcggagagt ttaatcccag caacggccgt     240
actaactaca tgagaaatt caagagcaag gccacactga ctgtagacaa atcctccagc     300
acagcctaca tgcaactcag cagcctgaca tctgaggact ctgcggtcta ttactgtgcc     360
agtcgggact atgattacga cggacggtac tttgactact ggggccaagg gaccacggtc     420
accgtctcct caggtggcgg tggctcgggc ggtggtgggt cgggtggtgg cggatctgac     480
atcgagctca cccagtctcc agcaatcatg tctgcatctc aggggagaa ggtcactatg     540 acctgcagtg ccagctcaag tgtaacttac atgtattggt accagcagaa gccaggatcc     600
tcccccagac tcctgattta tgacacatcc aacctggctt ctggagtccc tgttcgtttc     660
agtggcagtg gtctgggac ctcttactct ctcacaatca gccgaatgga ggctgaagat     720
gctgccactt attactgcca gcagtggagt agtcacatat tcacgttcgg ctcggggaca     780
gaactcgaga tcaaacgggt cgagcggagg cggttcagga ggcggttcag gaggtggctc     840
gagcggaggc ggttcaaagt tcaccatagt ttttccacac aaccaaaaag gaaactggaa     900
aaatgttcct tctaattacc attattgccc gtcaagctca gatttaaatt ggcataatga     960
cttaataggc acagccatac aagtcaaaat gcccaagagt cacaaggcta ttcaagcaga    1020
cggttggatg tgtcatgctt ccaaatgggt cactacttgt gatttccgct ggtatggacc    1080
gaagtatata acacagtcca tccgatcctt cactccatct gtagaacaat gcaaggaaag    1140
cattgaacaa cgaaacaag gaacttggct gaatccaggc ttccctcctc aaagttgtgg    1200
atatgcaact gtgacggatg ccgaagcagt gattgtccag gtgactcctc accatgtgct    1260
ggttgatgaa tacacaggag aatggggttga ttcacagttc atcaacggaa atgcagcaa    1320 ttacatatgc cccactgtcc ataactctac aacctggcat tctgactata aggtcaaagg    1380
gctatgtgat tctaacctca tttccatgga catcaccttc ttctcagagg acggagagct    1440
atcatccctg ggaaaggagg gcacagggtt cagaagtaac tactttgctt atgaaactgg    1500
aggcaaggcc tgcaaaatgc aatactgcaa gcattgggga tcagactcc atcaggtgt    1560 ctggttcgag atggctgata aggatctctt tgctgcagcc agattccctg aatgcccaga    1620
agggtcaagt atctctgctc catctcagac ctcagtggat gtaagtctaa ttcaggacgt    1680
tgagaggatc ttggattatt ccctctgcca agaaacctgg agcaaaatca gagcgggtct    1740
tccaatctct ccagtggatc tcagctatct tgctcctaaa aacccaggaa ccggtcctgc    1800
tttcaccata atcaatggta ccctaaaata ctttgagacc agatacatca gagtcgatat    1860
tgctgctcca atcctctcaa gaatggtcgg aatgatcagt ggaactacca cagaaaggga    1920
actgtgggat gactgggcac catatgaaga cgtggaaatt ggacccaatg gagttctgag    1980
```

```
gaccagttca ggatataagt ttcctttata catgattgga catggtatgt tggactccga    2040
tcttcatctt agctcaaagg ctcaggtgtt cgaacatcct cacattcaag acgctgcttc    2100
gcaacttcct gatgatgaga gtttattttt tggtgatact gggctatcca aaaatccaat    2160
cgagcttgta aaggttggt tcagtagttg aaaagctct attgcctctt ttttctttat      2220
catagggtta atcattggac tattcttggt tctccgagtt ggtatccatc tttgcattaa    2280
attaaagcac accaagaaaa gacagattta tacagacata gagatgaacc gacttggaaa    2340
gtaa                                                                 2344
```

<210> SEQ ID NO 10
<211> LENGTH: 780
<212> TYPE: PRT
<213> ORGANISM: Artificial Sequence
<220> FEATURE:
<223> OTHER INFORMATION: scFvEGFR-VSV-G (Signal sequence of VSV-G-His-Tag-scFvEGFR-Linker-VSV-G)

<400> SEQUENCE: 10

```
Met Lys Cys Leu Leu Tyr Leu Ala Phe Leu Phe Ile Gly Val Asn Cys
1               5                   10                  15

His His His His His His Ala Glu Val Gln Leu Gln Gln Ser Gly Ala
            20                  25                  30

Glu Leu Val Lys Pro Gly Ala Ser Val Lys Leu Ser Cys Lys Ala Ser
        35                  40                  45

Gly Tyr Thr Phe Thr Ser His Trp Met His Trp Val Lys Gln Arg Ala
    50                  55                  60

Gly Gln Gly Leu Glu Trp Ile Gly Glu Phe Asn Pro Ser Asn Gly Arg
65                  70                  75                  80

Thr Asn Tyr Asn Glu Lys Phe Lys Ser Lys Ala Thr Leu Thr Val Asp
                85                  90                  95

Lys Ser Ser Ser Thr Ala Tyr Met Gln Leu Ser Ser Leu Thr Ser Glu
            100                 105                 110

Asp Ser Ala Val Tyr Tyr Cys Ala Ser Arg Asp Tyr Asp Tyr Asp Gly
        115                 120                 125

Arg Tyr Phe Asp Tyr Trp Gly Gln Gly Thr Thr Val Thr Val Ser Ser
    130                 135                 140

Gly Gly Gly Gly Ser Gly Gly Gly Ser Gly Gly Gly Ser Asp
145                 150                 155                 160

Ile Glu Leu Thr Gln Ser Pro Ala Ile Met Ser Ala Ser Pro Gly Glu
                165                 170                 175

Lys Val Thr Met Thr Cys Ser Ala Ser Ser Ser Val Thr Tyr Met Tyr
            180                 185                 190

Trp Tyr Gln Gln Lys Pro Gly Ser Ser Pro Arg Leu Leu Ile Tyr Asp
        195                 200                 205

Thr Ser Asn Leu Ala Ser Gly Val Pro Val Arg Phe Ser Gly Ser Gly
    210                 215                 220

Ser Gly Thr Ser Tyr Ser Leu Thr Ile Ser Arg Met Glu Ala Glu Asp
225                 230                 235                 240

Ala Ala Thr Tyr Tyr Cys Gln Gln Trp Ser Ser His Ile Phe Thr Phe
                245                 250                 255

Gly Ser Gly Thr Glu Leu Glu Ile Lys Arg Val Glu Arg Arg Arg Phe
            260                 265                 270

Gly Gly Gly Ser Gly Gly Gly Ser Ser Gly Gly Gly Ser Lys Phe Thr
        275                 280                 285
```

```
Ile Val Phe Pro His Asn Gln Lys Gly Asn Trp Lys Asn Val Pro Ser
290                 295                 300

Asn Tyr His Tyr Cys Pro Ser Ser Asp Leu Asn Trp His Asn Asp
305                 310                 315                 320

Leu Ile Gly Thr Ala Ile Gln Val Lys Met Pro Lys Ser His Lys Ala
            325                 330                 335

Ile Gln Ala Asp Gly Trp Met Cys His Ala Ser Lys Trp Val Thr Thr
                340                 345                 350

Cys Asp Phe Arg Trp Tyr Gly Pro Lys Tyr Ile Thr Gln Ser Ile Arg
            355                 360                 365

Ser Phe Thr Pro Ser Val Glu Gln Cys Lys Glu Ser Ile Glu Gln Thr
370                 375                 380

Lys Gln Gly Thr Trp Leu Asn Pro Gly Phe Pro Pro Gln Ser Cys Gly
385                 390                 395                 400

Tyr Ala Thr Val Thr Asp Ala Glu Ala Val Ile Val Gln Val Thr Pro
            405                 410                 415

His His Val Leu Val Asp Glu Tyr Thr Gly Glu Trp Val Asp Ser Gln
                420                 425                 430

Phe Ile Asn Gly Lys Cys Ser Asn Tyr Ile Cys Pro Thr Val His Asn
            435                 440                 445

Ser Thr Thr Trp His Ser Asp Tyr Lys Val Lys Gly Leu Cys Asp Ser
450                 455                 460

Asn Leu Ile Ser Met Asp Ile Thr Phe Phe Ser Glu Asp Gly Glu Leu
465                 470                 475                 480

Ser Ser Leu Gly Lys Glu Gly Thr Gly Phe Arg Ser Asn Tyr Phe Ala
            485                 490                 495

Tyr Glu Thr Gly Gly Lys Ala Cys Lys Met Gln Tyr Cys Lys His Trp
                500                 505                 510

Gly Val Arg Leu Pro Ser Gly Val Trp Phe Glu Met Ala Asp Lys Asp
            515                 520                 525

Leu Phe Ala Ala Ala Arg Phe Pro Glu Cys Pro Glu Gly Ser Ser Ile
530                 535                 540

Ser Ala Pro Ser Gln Thr Ser Val Asp Val Ser Leu Ile Gln Asp Val
545                 550                 555                 560

Glu Arg Ile Leu Asp Tyr Ser Leu Cys Gln Glu Thr Trp Ser Lys Ile
            565                 570                 575

Arg Ala Gly Leu Pro Ile Ser Pro Val Asp Leu Ser Tyr Leu Ala Pro
                580                 585                 590

Lys Asn Pro Gly Thr Gly Pro Ala Phe Thr Ile Ile Asn Gly Thr Leu
            595                 600                 605

Lys Tyr Phe Glu Thr Arg Tyr Ile Arg Val Asp Ile Ala Ala Pro Ile
610                 615                 620

Leu Ser Arg Met Val Gly Met Ile Ser Gly Thr Thr Thr Glu Arg Glu
625                 630                 635                 640

Leu Trp Asp Asp Trp Ala Pro Tyr Glu Asp Val Glu Ile Gly Pro Asn
            645                 650                 655

Gly Val Leu Arg Thr Ser Ser Gly Tyr Lys Phe Pro Leu Tyr Met Ile
                660                 665                 670

Gly His Gly Met Leu Asp Ser Asp Leu His Leu Ser Ser Lys Ala Gln
            675                 680                 685

Val Phe Glu His Pro His Ile Gln Asp Ala Ala Ser Gln Leu Pro Asp
690                 695                 700
```

```
Asp Glu Ser Leu Phe Phe Gly Asp Thr Gly Leu Ser Lys Asn Pro Ile
705                 710                 715                 720

Glu Leu Val Glu Gly Trp Phe Ser Ser Trp Lys Ser Ser Ile Ala Ser
                725                 730                 735

Phe Phe Phe Ile Ile Gly Leu Ile Ile Gly Leu Phe Leu Val Leu Arg
                740                 745                 750

Val Gly Ile His Leu Cys Ile Lys Leu Lys His Thr Lys Lys Arg Gln
                755                 760                 765

Ile Tyr Thr Asp Ile Glu Met Asn Arg Leu Gly Lys
                770                 775                 780

<210> SEQ ID NO 11
<211> LENGTH: 69
<212> TYPE: DNA
<213> ORGANISM: Artificial Sequence
<220> FEATURE:
<221> NAME/KEY: source
<222> LOCATION: 1..69
<223> OTHER INFORMATION: /mol_type="unassigned DNA"
      /note="MfeI-His-tag sense primer"
      /organism="Artificial Sequence"

<400> SEQUENCE: 11
gcgaccaatt gccatcatca tcatcatcat gcccaggtca agctgcagga gtggactgaa    60
ctggcaaag                                                            69

<210> SEQ ID NO 12
<211> LENGTH: 70
<212> TYPE: DNA
<213> ORGANISM: Artificial Sequence
<220> FEATURE:
<221> NAME/KEY: source
<222> LOCATION: 1..70
<223> OTHER INFORMATION: /mol_type="unassigned DNA"
      /note="antisense primer, including half a linker sequence and
      harbouring an XhoI site "
      /organism="Artificial Sequence"

<400> SEQUENCE: 12
gtaatctcga gccacctcct gaaccgcctc ccgtttgat ttccagcttg gtgccacacc     60
gaacgtggcg                                                           70

<210> SEQ ID NO 13
<211> LENGTH: 62
<212> TYPE: DNA
<213> ORGANISM: Artificial Sequence
<220> FEATURE:
<221> NAME/KEY: source
<222> LOCATION: 1..62
<223> OTHER INFORMATION: /mol_type="unassigned DNA"
      /note="sense primer, including half a linker sequence"
      /organism="Artificial Sequence"

<400> SEQUENCE: 13
gttatctcga gcggaggcgg ttcaaagttc accatagttt ttccacacaa caaagaaac     60 tg                                                                   62

<210> SEQ ID NO 14
<211> LENGTH: 49
<212> TYPE: DNA
<213> ORGANISM: Artificial Sequence
```

```
<220> FEATURE:
<221> NAME/KEY: source
<222> LOCATION: 1..49
<223> OTHER INFORMATION: /mol_type="unassigned DNA"
      /note="antisense primer"
      /organism="Artificial Sequence"

<400> SEQUENCE: 14
gtattaccgg ttcctgggtt tttaggagca agatagctga gatccactg            49
```

PSEUDOTYPED LENTIVIRAL VECTORS

The present invention relates to a nucleic acid molecule comprising or consisting of a nucleic acid sequence encoding the vesicular stomatitis virus envelope glycoprotein (VSV-G) linked to a (poly)peptide comprising or consisting of a cell membrane-binding domain, said nucleic acid sequence comprising in 5' to 3' direction (a) a first sequence segment encoding an endoplasmic reticulum (ER) signal sequence; (b) a second sequence segment encoding said (poly)peptide comprising or consisting of a cell membrane-binding domain; (c) a third sequence segment encoding a linker; and (d) a fourth sequence segment encoding said VSV-G. Further, the invention relates to a vector comprising the nucleic acid molecule of the invention, a host cell comprising said vector or nucleic acid molecule, the polypeptide encoded by said nucleic acid molecule and a method of producing the polypeptide encoded by said nucleic acid molecule. In addition, the invention relates to a pseudotyped lentiviral vector particle, a method of transducing a cell as well as a kit comprising various combinations of the nucleic acid molecule, vectors, polypeptides and host cells of the invention.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Lentiviral expression vectors deliver stable gene expression and have become important tools for research and gene therapeutic applications. They enable the integration of genes of interest into the genome of a broad range of both dividing and non-dividing target cells [1]. Gammaretroviral and lentiviral vectors have been used successfully in several clinical gene therapy trials. Clinical applications of third generation self-inactivating lentiviruses with enhanced safety profile are expected to increase in number with recent success reported for gene therapy of severe combined immunodeficiency (SCID), and in tumour therapy for transfer of chimeric T-cell receptors [2-5].

Lentivirus vectors are often pseudotyped with vesicular stomatitis virus envelope glycoprotein (VSV-G), which binds the ubiquitously expressed LDL receptor [6]. VSV-G pseudotyped lentivirus vectors possess superior mechanical stability, which allows spinoculation and production of high-titer vector stocks [7]. The VSV-G protein is directed to the endoplasmatic reticulum by a signal sequence (SS), where it is glycosylated and forms trimers which are subsequently integrated into the cell membrane. Alterations in the protein structure of VSV-G commonly lead to inappropriate processing and unstable lentiviruses [8]. Despite the advances in methods for cell transduction, low transduction rates have been reported for several cell types, such as e.g. lymphoid lineage cells including primary T-cells and lymphoma cells, and some epithelial cell lines [4, 9]. These low transduction rates have the drawback that they lead to the necessity to use high multiplicity of infections (MOIs). In order to increase contact time and lentiviral uptake rates, genetic modification of the lentiviral VSV-G envelope for specific antigen binding has been reported [10-13]. Whole antibodies or antibody fragments may function as high affinity connectors between viral and cellular membranes, thereby opening the possibility of enhancing the transduction efficiency. However, previous attempts to fuse an N-terminal fusion of an scFv to VSV-G, as described in [14], led to impaired lentiviral vectors that lost their transduction activity. Thus, alternative approaches were developed that aimed at modifying the surface of lentiviral vectors with a smaller antibody-binding ZZ domain derived from *Staphylococcus* protein A fused to VSV-G [12]. Whereas this approach proved successful in vitro, it is nonetheless less advantageous for the development of clinical protocols because two reagents, the modified lentiviral vector and the respective antibodies, need to be approved and provided in clinical grade and combined to form the active therapeutic agent.

Thus, despite the fact that a lot of effort has been invested into methods to establish alternative and/or improved means and methods for transducing cells, there is still a need to provide such methods.

This need is addressed by the provision of the embodiments characterised in the claims.

Accordingly, the present invention relates to a nucleic acid molecule comprising or consisting of a nucleic acid sequence encoding the vesicular stomatitis virus envelope glycoprotein (VSV-G) linked to a (poly)peptide comprising or consisting of a cell membrane-binding domain, said nucleic acid sequence comprising in 5' to 3' direction (a) a first sequence segment encoding an endoplasmic reticulum (ER) signal sequence; (b) a second sequence segment encoding said (poly)peptide comprising or consisting of a cell membrane-binding domain; (c) a third sequence segment encoding a linker; and (d) a fourth sequence segment encoding said VSV-G.

The articles "a" and "an" are used herein to refer to one or more (i.e. to at least one) of the grammatical object of the article.

In accordance with the present invention, nucleic acid molecules, which are also referred to herein as polynucleotides or nucleic acid sequences, include DNA, such as cDNA or genomic DNA, and RNA. It is understood that the term "RNA" as used herein comprises all forms of RNA including mRNA, tRNA and rRNA but also genomic RNA, such as in case of RNA of RNA viruses. Preferably, embodiments reciting "RNA" are directed to mRNA.

Further included are nucleic acid mimicking molecules known in the art such as synthetic or semi-synthetic derivatives of DNA or RNA and mixed polymers, both sense and antisense strands. They may contain additional non-natural or derivatized nucleotide bases, as will be readily appreciated by those skilled in the art. Such nucleic acid mimicking molecules or nucleic acid derivatives according to the invention include peptide nucleic acid (PNA), phosphorothioate nucleic acid, phosphoramidate nucleic acid, 2'-O-methoxyethyl ribonucleic acid, morpholino nucleic acid, hexitol nucleic acid (HNA) and locked nucleic acid (LNA), an RNA derivative in which the ribose ring is constrained by a methylene linkage between the 2'-oxygen and the 4'-carbon (see, for example, Braasch and Corey, Chemistry & Biology 8, 1-7 (2001)). PNA is a synthetic DNA-mimic with an amide backbone in place of the sugar-phosphate backbone of DNA or RNA, as described by Nielsen et al., Science 254:1497 (1991); and Egholm et al., Nature 365:666 (1993).

In a preferred embodiment, at least the nucleic acid sequences specifically recited in options (a) to (d) are DNA. In an even more preferred embodiment, the entire nucleic acid molecule of the invention is DNA.

The nucleic acid molecules of the invention may be of natural as well as of synthetic or semi-synthetic origin. Thus, the nucleic acid molecules may, for example, be nucleic acid molecules that have been synthesized according to conventional protocols of organic chemistry. The person skilled in the art is familiar with the preparation and the use of such nucleic acid molecules (see, e.g., Sambrook and Russel "Molecular Cloning, A Laboratory Manual", Cold Spring Harbor Laboratory, N.Y. (2001)).

The term comprising, as used herein, denotes that further sequences, components and/or method steps can be included in addition to the specifically recited sequences, components and/or method steps. However, this term also encompasses that the claimed subject-matter consists of exactly the recited sequences, components and/or method steps.

In those embodiments where the nucleic acid molecule comprises (rather than consists of) the recited sequence, additional nucleotides extend over the specific sequence either on the 5' end or the 3' end, or both. Those additional nucleotides may be of heterologous or homologous nature. In the case of homologous sequences, these sequences may comprise up to 1500 nucleotides at the 5' and/or the 3' end, such as e.g. up to 1000 nucleotides, such as up to 900 nucleotides, more preferably up to 800 nucleotides, such as up to 700 nucleotides, such as e.g. up to 600 nucleotides, such as up to 500 nucleotides, even more preferably up to 400 nucleotides, such as up to 300 nucleotides, such as e.g. up to 200 nucleotides, such as up to 100 nucleotides, more preferably up to 50 nucleotides, such as up to 40 nucleotides such as e.g. up to 30 nucleotides, such as up to 20 nucleotides, more preferably up to 10 nucleotides and most preferably up to 5 nucleotides at the 5' and/or the 3' end. The term "up to [ . . . ] nucleotides", as used herein, relates to a number of nucleotides that includes any integer below and including the specifically recited number. For example, the term "up to 5 nucleotides" refers to any of 1, 2, 3, 4 and 5 nucleotides. Furthermore, in the case of homologous sequences, those embodiments do not include complete genomes or complete chromosomes.

Additional heterologous sequences may, for example, include heterologous promoters which are operatively linked to the coding sequences of the invention, as well as further regulatory nucleic acid sequences well known in the art and described in more detail herein below.

The nucleic acid sequence comprised in or making up the nucleic acid molecule of the present invention encodes the vesicular stomatitis virus envelope glycoprotein linked to a (poly)peptide comprising or consisting of a cell membrane-binding domain. As such, the nucleic acid sequence and, thus, the nucleic acid molecule of the present invention encode a fusion protein, which is also referred to herein as "the fusion protein of the invention".

In accordance with the present invention, the nucleic acid molecule is made up of at least four sequences as defined in options (a) to (d), wherein the order of these four nucleic acid sequences is as indicated from 5' to 3', i.e. the first nucleic acid sequence is that of (a), followed by (b), followed by (c) which in turn is followed by (d).

The first sequence in accordance with option (a) is a nucleic acid sequence encoding an endoplasmic reticulum (ER) signal sequence. An ER signal sequence is a short peptide sequence present at the N-terminus of newly synthesized proteins. Upon ignition of mRNA translation, this sequence is the first sequence to be translated and the emerging signal sequence of the nascent protein binds to signal recognition particles (SRPs). Binding of SRPs to the ER signal sequence pauses translation and leads to the translocation of the SRP-signal sequence-mRNA-ribosome complex to the ER, where the SRP recognizes and docks onto a receptor on the ER membrane (RER). The signal sequence is subsequently inserted into the RER and crosses the membrane, such that translation continues with the emerging polypeptide chain being pulled into the ER lumen.

Sequence motifs of ER signal sequences are well known in the art and have been described, e.g., in Lemberg and Martoglio or in Schwartz [45, 46]. Thus, the skilled person is aware of suitable naturally occurring ER signal sequences or is in the position to generate artificial, i.e. not naturally occurring, ER signal sequences exhibiting the above described functionality, which can be employed in accordance with the invention.

Preferably, naturally occurring ER signal sequences are used, more preferably a viral ER signal sequence or ER signal sequence endogenous to the cell system used for the production of the fusion protein encoded by the nucleic acid molecule of the invention. In the case of viral ER signal sequences, it is preferred that it originates from *Rhabdoviridae*, more preferred from the genus *Vesiculovirus*. Most preferably the ER signal sequence is the ER signal sequence that endogenously mediates translocation to the ER of the VSV-G employed in accordance with option (d).

The second sequence segment in accordance with option (b) is a nucleic acid sequence encoding a (poly)peptide comprising or consisting of a cell membrane-binding domain.

The term "(poly)peptide" in accordance with the present invention relates to polypeptides as well as peptides. The term "polypeptide", as used herein interchangeably with the term "protein", describes linear molecular chains of amino acids, including single chain proteins or their fragments, containing more than 30 amino acids, whereas the term "peptide" as used herein describes a group of molecules consisting of up to 30 amino acids. (Poly)peptides may further form oligomers consisting of at least two identical or different molecules. The corresponding higher order structures of such multimers are, correspondingly, termed homo- or heterodimers, homo- or heterotrimers etc. Such multimers also fall under the definition of the term "(poly)peptide". The terms "polypeptide" and "peptide" also refer to naturally modified polypeptides/peptides where the modification is effected e.g. by glycosylation, acetylation, phosphorylation and similar modifications which are well known in the art.

In accordance with the present invention, the nucleic acid molecule encodes "a (poly)peptide comprising or consisting of a cell membrane-binding domain". The term "cell membrane" and its scientific meaning relating to structure and function are well-known in the art [47, 48] and is used accordingly in the context of the present invention. The "cell membrane-binding domain" in accordance with the present invention can be any amino acid sequence capable of directly binding to a cell membrane. Binding domains which only indirectly bind to the cell membrane via intermediate molecules are specifically excluded.

The function of the cell membrane-binding domain within the fusion protein of the invention is to act as a connector between a viral particle expressing the fusion protein of the invention and a target cell that is to be transduced by said viral particle. Thus, it will be appreciated that a cell membrane-binding domain is to be chosen that is capable of binding to the cell membrane of the target cell of interest. Preferably, the cell membrane-binding domain is capable of binding to a mammalian target cell membrane. More preferably, the cell membrane-binding domain is capable of binding to a cell membrane of a human target cell such as, e.g. progenitor cells, diseased cells, primary cell lines, epithelial cell, endothelial cells, neuronal cells, lymphoid lineage cells, stem cells or tumor cells.

The term "binding", in this context, refers to the capability of the domain to associate with the cell membrane, for example via covalent or non-covalent interactions. A "covalent" interaction is a form of chemical bonding that is characterized by the sharing of pairs of electrons between atoms, or between atoms and other covalent bonds. Covalent bonding includes many kinds of interaction well-known in the art such as, e.g., σ-bonding, π-bonding, metal to non-metal bonding, agostic interactions and three-center two-electron bonds. A "non-covalent" bond is a chemical bond that does not involve the sharing of pairs of electrons. Non-covalent bonds are critical in maintaining the three-dimensional structure of large molecules, such as proteins and nucleic acids, and are involved in many biological processes in which molecules bind specifically but transiently to one another. There are several types of non-covalent bonds, such as hydrogen bonding, ionic interactions, Van-der-Waals interactions, charge-charge, charge-dipole, dipole-dipole bonds and hydrophobic bonds. Non-covalent interactions often involve several different types of non-covalent bonds working in concert, e.g., to keep a ligand in position on a target binding site on the cell membrane. An interaction may occur with a group such as a charge or a dipole, which may be present many times at the surface of the cell membrane.

Preferably, the interaction (i.e. the binding) occurs at a defined site (involves a specific cell membrane constituent/epitope) of the cell membrane, and goes along with the formation of at least one interaction, preferably the formation of a network of several specific interactions. Even more preferably, the binding is specific for the target cell, i.e. the binding occurs at the cell membrane of the target cell but not, or not significantly, at the cell membrane of a non-target cell.

The structure of the domain is not limited as long as it complies with the function of binding, preferably, specific binding, to the cell membrane. Various cell membrane-binding domains are known in the art including, without limitation, antibodies and fragments thereof, protein scaffolds as well as protein domains with cell-binding properties, such as i.e. fibronectin-derived (poly)peptides [49] and (poly)peptides with heparin-binding activity.

The term "antibody" as used in accordance with the present invention comprises polyclonal and monoclonal antibodies, as well as derivatives or fragments thereof, which still retain their binding specificity. Antibody fragments or derivatives comprise, inter alia, single domain antibodies, nanobodies, camelid VHH fragments, and VNAR fragments from cartilaginous fishes Fab or Fab' fragments as well as Fd, F(ab')$_2$, Fv or scFv fragments; see, for example Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" also includes embodiments such as chimeric (human constant domain, non-human variable domain), single chain and humanized (human antibody with the exception of non-human CDRs) antibodies. Preferably, the antibody is a humanized antibody.

Various techniques for the production of antibodies are well known in the art and described, e.g. in Altshuler et al., 2010 (Altshuler E P, Serebryanaya D V, Katrukha A G. 2010, Biochemistry (Mosc)., vol. 75(13), 1584). Thus, polyclonal antibodies can be obtained from the blood of an animal following immunisation with an antigen in mixture with additives and adjuvants and monoclonal antibodies can be produced by any technique which provides antibodies produced by continuous cell line cultures. Examples for such techniques are described, e.g. in Harlow E and Lane D, Cold Spring Harbor Laboratory Press, 1988; Harlow E and Lane D, Using Antibodies: A Laboratory Manual, Cold Spring Harbor Laboratory Press, 1999 and include the hybridoma technique originally described by Köhler and Milstein, 1975, the trioma technique, the human B-cell hybridoma technique (see e.g. Kozbor D, 1983, Immunology Today, vol. 4, 7; Li J, Sai T, Berger M, Chao Q, Davidson D, Deshmukh G, Drozdowski B, Ebel W, Harley S, Henry M, Jacob S, Kline B, Lazo E, Rotella F, Routhier E, Rudolph K, Sage J, Simon P, Yao J, Zhou Y, Kavuru M, Bonfield T, Thomassen M J, Sass P M, Nicolaides N C, Grasso L., 2006, PNAS, vol. 103(10), 3557) and the EBV-hybridoma technique to produce human monoclonal antibodies (Cole et al., 1985, Alan R. Liss, Inc, 77-96). Furthermore, recombinant antibodies may be obtained from monoclonal antibodies or can be prepared de novo using various display methods such as phage, ribosomal, mRNA, or cell display. A suitable system for the expression of the recombinant (humanised) antibodies may be selected from, for example, bacteria, yeast, insects, mammalian cell lines or transgenic animals or plants (see, e.g., U.S. Pat. No. 6,080,560; Holliger P, Hudson P J. 2005, Nat Biotechnol., vol. 23(9), 11265). Further, techniques described for the production of single chain antibodies (see, inter alia, U.S. Pat. No. 4,946,778) can be adapted to produce single chain antibodies specific for the target of this invention. Surface plasmon resonance as employed in the BIAcore system can be used to increase the efficiency of phage antibodies. Preferably, the antibody is selected from the group consisting of an anti-EGFR antibody, an anti-CD30 antibody, an anti-CD34 antibody, an anti-CD3 antibody, an anti-CD4 antibody, an anti-CD19 antibody, an anti-CD20 antibody or an anti-CD44 antibody. More preferably, the antibody is an anti-EGFR antibody or an anti-CD30 antibody. The epidermal growth factor receptor (EGFR) is known to be pre-dominantly expressed on epithelial, and CD30 expressed on lymphoma cells, respectively [15-18]. Various antibody fragments with high affinities against EGFR and CD30 are available and were previously used in vitro and in vivo [19-21]. Preferably, the at least one affinity-reagent may be one of the anti-EGFR or an anti-CD30 antibodies employed in the examples. Suitable scFv antibodies against CD30 and EGFR are known in the art and have been described, e.g. in Klimka et al. [63] and Kettleborough et al. [64].

The term "protein scaffolds" is well known in the art and relates to a new generation of receptor proteins that are derived from small and robust non-immunoglobulin "scaffolds" that can be equipped with prescribed binding functions using methods of combinatorial protein design (Gebauer and Skerra (2009) Engineered protein scaffolds as next-generation antibody therapeutics. Curr Opin Chem Biol, 13, 245-255.). Preferred, but non-limiting, examples of engineered protein scaffolds are protein scaffolds for the development of drug candidates for therapy or in vivo diagnostics, and include adnectins, affibodies, anticalins, DARPins and engineered Kunitz-type inhibitors, as detailed further below.

The nucleic acid molecule of option (b) can either encode a (poly)peptide comprising said cell membrane-binding domain or can encode a (poly)peptide consisting of said cell membrane-binding domain. In the first option, the cell membrane-binding domain is part of a larger molecule, such as e.g. an antibody. In the latter option, the (poly)peptide is per se a cell membrane-binding domain. Examples for this option include, without being limiting, the protein scaffolds described herein above. Irrespective of whether the cell membrane-binding domain is part of a larger molecule or is per se a cell membrane-binding domain it will be appreciated that it is in any case part of the protein encoded by the nucleic acid molecule of the invention, i.e. containing at least the additional segments (a), (c) and (d).

The third sequence segment in accordance with option (c) encodes a "linker". The term "linker", as used in accordance with the present invention, relates to a sequel of amino acids (i.e. peptide linkers). In accordance with the present invention, the linker is located between the amino acid sequence encoded by the second sequence segment and the amino acid sequence encoded by the fourth sequence segment, thereby connecting (linking) these two sequences in the translated protein.

The linker as envisaged by the present invention is a (poly)peptide linker of at least 3 amino acids in length. In a preferred embodiment, the linker is 3 to 100 amino acids in length, more preferably, the linker is 5 to 50 amino acids in length and even more preferably, the linker is 10 to 20 amino acids in length. Most preferably, the linker is 13 amino acids in length. In an alternative, or additional, embodiment, the linker extends the distance of the cell membrane binding domain from the lentivirus vector surface to about 5 to 100 Å, more preferably from about 5 to 75 Å, and even more preferably from about 5 to 50 Å. Most preferably, the linker extends the distance of the cell binding domain to about 30 Å. Means and methods for determining the distance of the cell membrane binding domain from the lentivirus vector surface are well known in the art and include, without being limiting, the analysis of three-dimensional structures of the fusion protein, secondary/tertiary structure prediction and homology modelling as well as sequence alignments.

It will be appreciated that the linker serves to physically separate nucleic acid segments, e.g. the segments (b) and (d) of the nucleic acid molecule of the invention. As is known in the art, the nature, i.e. the length and/or amino acid sequence of the linker may affect the expressed fusion protein, e.g. it may modify or enhance the stability and/or solubility of the expressed fusion protein or may have sterical effects influencing interactions with other molecules or multimerization. Thus, preferred linkers should not interfere with the correct expression and folding of the encoded polypeptide and the biological function of the VSV-G and the cell membrane-binding domain, as it is a prerequisite that the polypeptide of the invention maintains the capacity to bind to target cells. Accordingly, the linker has to be sufficiently long and/or flexible to still enable these properties. Thus, the length and sequence of a linker can be varied based on the actual composition, i.e. the choice of sequence segments of the molecule of the invention. Furthermore, preferred linkers should adopt a flexible conformation and should have minimal hydrophobic or charged character, to avoid interaction with the functional protein domains and/or solvent. Preferably, the linker is chosen to be a moiety capable of avoiding detection by the immune system. The skilled person knows how to design appropriate linker molecules based on his/her common knowledge. For example, peptide linkers can be chosen from the LIP (Loops in Proteins) database (Michalsky et al., 2003 [50]) obtained commercially (see, for example, the catalogue from Glen Research, 22825 Davis Drive, Sterling, Va., 20164 USA).

The skilled person is well aware of methods to test the suitability of different linkers. For example, the suitability of a linker can easily be tested by comparing the virus yield and/or transduction rates of the lentiviral vector of the invention as described herein below (see also example 4).

Preferably, the linker is a flexible linker comprising e.g. the amino acids glycine, aspargine and/or serine, preferably it comprises the amino acids glycine and serine or alanine and serine. More preferably, the linker comprises or consists of the amino acid sequence shown in SEQ ID NO:3. Even more preferably, the linker consists of the amino acid sequence shown in SEQ ID NO:3.

The fourth sequence segment in accordance with option (d) encodes the vesicular stomatitis virus envelope glycoprotein. The vesicular stomatitis virus (abbreviated herein as VSV) is also referred to as vesicular stomatitis Indiana virus (VSIV) and is a virus of the *Rhabdoviridae* family of group V (i.e. negative sense ssRNA) viruses. The virus, its hosts and the diseases triggered by infection with said virus are well-known in the art [51-53]. VSV-G is a transmembrane glycoprotein [6, 52] and is known to associate efficiently with immature, non-infectious, envelope-deficient retrovirus-like particles assembled by packaging cells to produce infectious, pseudotyped viruses in cell-free conditions in vitro. As such, the sequence of the VSV envelope glycoprotein is also well-known in the art and includes, in accordance with the invention, a cytoplasmic tail, a transmembrane domain and a membrane-proximal extracellular stem region (ectodomain or extracellular domain) that mediates efficient virus budding. VSV-G sequences have been described in the art, e.g., in [54] and the NCBI Reference number of the naturally occurring VSV-G is NP_955548.1 (NCBI Genome Project, 2000).

It will be appreciated that the first sequence segment in accordance with the present invention already encodes an ER signal sequence and, thus, the VSV-G encoded by the fourth sequence segment does, preferably, not comprise a further ER signal sequence. For the purposes of the invention, either a naturally occurring VSV-G sequence or a modified VSV-G sequence [55, 56] can be used. For example, the insertion of targeting peptides, such as RGD or the insertion of positively charged peptides (e.g. polylysine peptides (K7-K20), in permissive epitope insertion site (see [55 and 56]) of VSV-G can be used to achieve enhanced effects [57-60]. In case of employing a modified VSV-G sequence, it is important that the modification(s) do(es) not compromise the capability of the modified VSV-G to bind to the LDL receptor, and/or its capability to result in stable and correctly processed lentiviral vectors pseudotyped with said modified VSV-G sequence. Preferably, the modification is not in the transmembrane (e.g. ranging from position 426 to 466 in the VSV-G protein shown in SEQ ID NO:6) or in the cytoplasmic domain (e.g. ranging from position 467 to 495 in the VSV-G protein shown in SEQ ID NO: 6). Also preferred is that the modification is not in the region between amino acids 385 and 444 of the VSV-G glycoprotein shown in SEQ ID NO: 6, as that region has a propensity to form α-helices, suggesting that this region may be capable of interacting directly with membranes [62]. Preferably, the VSV-G sequence is not modified. In addition, it is specifically preferred that the N-terminal domain of VSV-G is directly fused to the linker, as defined herein above.

In accordance with the present invention, the sequence segments are arranged in 5' to 3' direction. Each sequence segment can follow the previous sequence segment without or with intermediate sequences. Alternatively, or additionally, terminal sequences may be added to the 5' and/or 3' end, as detailed herein above. For example, it is explicitly envisaged herein that a fifth sequence segment (i.e. 3' of the fourth segment) encoding a detectable label is comprised in the nucleic acid molecule of the invention. An exemplary detectable label, as well as an exemplary intermittent sequence, can e.g. be a tag for later purification or detection purposes of either the nucleic acid molecule of the invention or the polypeptide encoded thereby. Non-limiting examples of tags include Strep-tags, chitin binding proteins (CBP), maltose binding proteins (MBP), glutathione-S-transferase (GST), FLAG-tags, HA-tags, Myc-tags, poly(His)-tags as well as derivatives thereof or epitope tags, such as e.g. the V5-tag, c-myc-tag and the HA-tag. All these tags as well as derivatives thereof are well known in the art and have been described, for example in Lichty J J et al. Comparison of affinity tags for protein purification Protein Expr Purif. 2005 May; 41 (1): 98-105. Preferably, if a tag is included in the fusion protein, the tag is a His-tag as shown in FIG. 1. Detectable labels further include, without being limiting, radioactive labels such as $^3$H, or $^{32}$P or fluorescent labels as well as reporter proteins. Labelling of nucleic acids is well understood in the art and described, for example, in Sambrook and Russel "Molecular Cloning, A Laboratory Manual", Cold Spring Harbor Laboratory, N.Y. (2001).

If intermediate sequences and/or terminal sequences are present, these are to be selected such that they do not compromise the integrity and functionality of the VSV-G fusion protein of the invention, in particular its use as part of a lentiviral vector resulting in an increased transfection efficiency of cells, preferably hard-to-transfect cells. The skilled person is aware of modifications that can adversely affect integrity and functionality of fusion proteins comprising cell membrane-binding domains on the basis of their scientific knowledge and is thereby capable of identifying suitable intermittent and/or terminal sequences, if required. Further, the skilled person can experimentally ascertain, e.g., on the basis of the experiments described herein, whether said integrity and functionality are compromised by the addition of intermittent and/or terminal sequences.

Preferably, no intermediate sequences are present between the second, third and fourth sequence segments, i.e. these sequence segments follow each other directly such that the sequence of the fusion protein corresponding to the second to fourth segment is made up of only the nucleotides belonging to said second, third and fourth sequence segment.

In accordance with the present invention, novel VSV-G fusion proteins were established containing N-terminal single-chain antibody fragments (scFv) directed against either the tumor antigen EGFR or CD30, wherein the VSV-G and the scFv are separated by a flexible linker. As is shown in the appended examples, high titer lentivirus vector (LV) preparations could be obtained using the scFv-modified VSV-G of the invention in specific ratios with wt-VSV-G. As also shown in the appended examples, production of lentiviral particles with VSV-G fusion proteins without a linker led to a strong decrease in virus yields and these virus particles failed to increase transduction rates of T47D cells. The present inventors thus conclude that a linker sequence between the cell membrane binding-domain and VSV-G is essential for the functionality of VSV-G fusion protein retargeted lentivirus particles.

So far, no successful attempts to fuse an N-terminal fusion of an scFv to VSV-G have been reported in the art. Instead, alternative approaches where pursued in the art, such as modifying the surface of lentiviral vectors with a smaller antibody-binding ZZ domain derived from *Staphylococcus* protein A fused to VSV-G [12]. This approach, however, requires that two reagents, the modified lentiviral vector and the respective antibodies, are approved for clinical use, are provided in clinical grade purity and are then combined to form the active therapeutic agent. Thus, the novel VSV-G fusion proteins of the present invention provide an improved means for the pseudotyping of LVs in order to prepare lentiviral particles having improved transduction efficiency at low MOIs and being suitable for the transduction of hard-to-transduce cells such as e.g. lymphoid lineage cells or tumor cells.

In a preferred embodiment of the nucleic acid molecule of the invention, the (poly)peptide comprising or consisting of a cell membrane binding-domain encoded by said second sequence segment is selected from the group consisting of a single chain antibody, a single domain antibody, a $V_HH$ antibody fragment, a VNAR single chain antibody and a protein scaffold.

The above recited types of antibodies include, as described herein above, embodiments such as chimeric (human constant domain, non-human variable domain) and humanised (human antibody with the exception of non-human CDRs) antibodies.

The term "protein scaffold", also used herein interchangeably with the term "engineered protein scaffold" is well known in the art and relates to a new generation of receptor proteins that are derived from small and robust non-immunoglobulin "scaffolds" that can be equipped with prescribed binding functions using methods of combinatorial protein design (Gebauer and Skerra (2009) Engineered protein scaffolds as next-generation antibody therapeutics. Curr Opin Chem Biol, 13, 245-255.). Preferred, but non-limiting, examples of engineered protein scaffolds include adnectins, affibodies, anticalins and DARPins.

"Adnectins" (also referred to as monobodies) in accordance with the present invention, are based on the 10th extracellular domain of human fibronectin III (10Fn3), which adopts an Ig-like b-sandwich fold of 94 residues with 2 to 3 exposed loops, but lacks the central disulphide bridge.

"Affibodies", in accordance with the present invention, are based on the Z-domain of staphylococcal protein A, a three-helix bundle of about 58 residues providing an interface on two of its a-helices.

The term "anticalins" as used herein refers to engineered proteins derived from lipocalins (Beste, G., Schmidt, F. S., Stibora, T., Skerra, A. (1999) Small antibody-like proteins with prescribed ligand specificities derived from the lipocalin fold. *PNAS*, 96, 1898-903). Anticalins possess an eight-stranded β-barrel which forms a highly conserved core unit among the lipocalins and naturally forms binding sites for ligands by means of four structurally variable loops at the open end. Anticalins, although not homologous to the IgG superfamily, show features that so far have been considered typical for the binding sites of antibodies: (i) high structural plasticity as a consequence of sequence variation and (ii) elevated conformational flexibility, allowing induced fit to targets with differing shape.

In accordance with the present invention, the term "DARPins" refers to designed ankyrin repeat domains (166 residues), which provide a rigid interface arising from typically three repeated b-turns. DARPins usually carry three repeats corresponding to an artificial consensus sequence, whereby six positions per repeat are randomized. Consequently, DARPins lack structural flexibility.

A "Kunitz domain peptide" is derived from the Kunitz domain of a Kunitz-type protease inhibitor such as, for example, bovine pancreatic trypsin inhibitor (BPTI), amyloid precursor protein (APP) or tissue factor pathway inhibitor (TFPI). Kunitz domains have a molecular weight of approximately 6 kDA and domains with the required target specificity can be selected by display techniques such as phage display (Gebauer and Skerra (2009) Engineered protein scaffolds as next-generation antibody therapeutics. Curr Opin Chem Biol, 13, 245-255.).

In a particularly preferred embodiment of the nucleic acid molecule of the invention, the (poly)peptide comprising or consisting of a cell membrane-binding domain encoded by said second sequence segment is a single chain antibody.

As regards the arrangement of the $V_L$ and $V_H$ domain in the immunoglobulin domain, the $V_L$ domain may be positioned N- or C-terminal of the $V_H$ domain. Accordingly, in the nucleic acid of the present invention, the nucleic acid encoding the $V_L$ domain may be positioned 5' or 3' of that encoding the $V_H$ domain. The skilled person is able to determine which arrangement of the $V_H$ and $V_L$ domains is more suitable for a specific scFv.

In a further preferred embodiment of the nucleic acid molecule of the invention, the (poly)peptide comprising or consisting of a cell membrane-binding domain binds specifically to one or more cell membrane constituents selected from the group consisting of glycolipids, phospholipids, oligosaccharides and proteins.

Glycolipids are lipids with a carbohydrate attached, which are present on cell membranes where they serve, amongst others, for cellular recognition. Non-limiting examples of glycolipids include glyceroglycolipids, glycosphingolipids and glycosylphosphatidylinositols.

Phospholipids are amphiphilic lipids that contain a phosphate group. The most commonly found phospholipids in the cell membrane are phosphatidylcholine (lecithine, abbreviated PC), phosphatidylethanolamine (cephalin, abbr. PE), phosphatidylserine (PS) and Sphingomyelins. Based on their chemical make-up, they are grouped into two groups, the glycerophospholipids having glycerine as their basic structure and the sphingomyelins, which are phosphate-containing sphingolipids derived from sphingosine.

Oligosaccharides are saccharide polymers containing a small number of simple sugars (monosaccharides). They are commonly found on the plasma membrane of animal cells where they, amongst others, play a role in cell-cell recognition.

As defined herein above, proteins are linear molecular chains of amino acids containing 30 amino acids or more. Preferred proteins in accordance with this embodiment are G-protein-coupled cellular receptors (GPCRs), cluster of differentiation (CD; also referred to as "cluster of designation" in the art) cell surface proteins, cell surface receptors or cell surface co-receptors.

In a further preferred embodiment of the nucleic acid molecule of the invention, (a) the first sequence segment encoding said ER signal sequence comprises or consists of the nucleic acid sequence as shown in SEQ ID NO:1 or a nucleic acid sequence having at least 60% identity to SEQ ID NO:1; (b) the third sequence segment encoding a linker comprises or consists of the nucleic acid sequence as shown in SEQ ID NO:3 or a nucleic acid sequence having at least 60% identity to SEQ ID NO:3; and/or (c) the fourth sequence segment encoding said VSV-G comprises or consists of the nucleic acid sequence as shown in SEQ ID NO:5 or a nucleic acid sequence having at least 60% identity to SEQ ID NO:5.

Accordingly, also encompassed by the present invention are nucleic acid molecules, nucleic acid sequences or sequence segments having at least 60% identity (such as at least 70%, preferably at least 80%, more preferred at least 90%, even more preferred at least 95% such as at least 98% and most preferred at least 99% identity) with the nucleic acid molecule depicted by the recited SEQ ID numbers.

Such variant molecules may be splice forms or homologous molecules from other species. It will be appreciated that these variant nucleic acid molecule nonetheless have to encode an amino acid sequence having the indicated functions, i.e. the sequence encoded by a variant of SEQ ID NO:1 has to be an ER signal sequence; the sequence encoded by a variant of SEQ ID NO:3 has to be a linker; and the sequence encoded by a variant of SEQ ID NO:5 has to encode a glycoprotein having VSV-G function as defined herein above.

In accordance with the present invention, the term "at least % identical to" in connection with nucleic acid molecules describes the number of matches ("hits") of identical nucleic acids of two or more aligned nucleic acid sequences as compared to the number of nucleic acid residues making up the overall length of the amino acid sequences (or the overall compared part thereof). In other terms, using an alignment, for two or more sequences or subsequences, the percentage of nucleic acid residues that are the same (e.g. at least 60% identity) may be determined, when the (sub) sequences are compared and aligned for maximum correspondence over a window of comparison, or over a designated region as measured using a sequence comparison algorithm as known in the art, or when manually aligned and visually inspected. Preferred nucleic acids in accordance with the invention are those where the described identity exists over a region that is at least 100 to 150 nucleotides in length, more preferably, over a region that is at least 200 to 400 nucleotides in length. More preferred nucleic acids in accordance with the present invention are those having the described sequence identity over the entire length of the nucleic acid molecule as described in (a) and (b) supra.

In one embodiment, the two sequences, when aligned, display the at least 60% identity over the same length, i.e. without either sequence extending at the 3' or the 5' end over the other sequence. In the alternative, if such an extension occurs, it is preferred that it does not exceed more than 30 nucleotides, more preferred not more than 15 nucleotides over either terminus of the other sequence.

It is well known in the art how to determine percent sequence identity between/among sequences using, for example, algorithms such as those based on CLUSTALW computer program (Thompson Nucl. Acids Res. 2 (1994), 4673-4680) or FASTA (Pearson and Lipman, Proc. Natl. Acad. Sci., 1988, 85; 2444). Although the FASTA algorithm typically does not consider internal non-matching deletions or additions in sequences, i.e., gaps, in its calculation, this can be corrected manually to avoid an overestimation of the % sequence identity. CLUSTALW, however, does take sequence gaps into account in its identity calculations. Also available to those having skill in this art are the BLAST and BLAST 2.0 algorithms (Altschul, Nucl. Acids Res., 1977, 25:3389). The BLASTN program for nucleic acid sequences uses as default a word length (W) of 11, an expectation (E) of 10, M=5, N=4, and a comparison of both strands. For amino acid sequences, the BLASTP program uses as default a word length (W) of 3, and an expectation (E) of 10. The BLOSUM62 scoring matrix (Henikoff, Proc. Natl. Acad. Sci., 1989, 89:10915) uses alignments (B) of 50, expectation (E) of 10, M=5, N=4, and a comparison of both strands. All those programs may be used for the purposes of the present invention. However, preferably the BLAST program is used.

Accordingly, all the nucleic acid molecules having the prescribed function and further having a sequence identity of at least 60% as determined with any of the above recited or further programs available to the skilled person and preferably with the BLAST program fall under the scope of the invention.

In a more preferred embodiment of the nucleic acid molecule of the invention, (a) the first sequence segment encoding said ER signal sequence comprises or consists of the nucleic acid sequence as shown in SEQ ID NO:1; (b) the third sequence segment encoding a linker comprises or consists of the nucleic acid sequence as shown in SEQ ID NO:3; and/or (c) the fourth sequence segment encoding said VSV-G comprises or consists of the nucleic acid sequence as shown in SEQ ID NO:5.

In an even more preferred embodiment of the nucleic acid molecule of the invention, the nucleic acid molecule has the overall nucleic acid sequence of SEQ ID NO: 7 or SEQ ID NO: 9.

The present invention further relates to a vector comprising the nucleic acid molecule of the invention.

Preferably, the vector is a plasmid, cosmid, virus, bacteriophage or another vector used e.g. conventionally in genetic engineering. The nucleic acid molecule of the present invention may be inserted into several commercially available vectors suitable for the expression of eukaryotic proteins. Non-limiting examples include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pCINeo (Promega).

The nucleic acid molecule of the present invention referred to above may also be inserted into vectors such that a translational fusion with another polynucleotide is generated. The other polynucleotide may encode a protein which may e.g. increase the solubility and/or facilitate the purification of the fusion protein. Non-limiting examples include pET32, pET41, pET43.

For vector modification techniques, see Sambrook and Russell "Molecular Cloning, A Laboratory Manual", Cold Spring Harbor Laboratory, N.Y. (2001). Generally, vectors can contain one or more origin of replication (ori) and inheritance systems for cloning or expression, one or more markers for selection in the host, e. g., antibiotic resistance, and one or more expression cassettes. Suitable origins of replication (ori) include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression of the coding sequences are well known to those skilled in the art. These elements comprise regulatory sequences ensuring the initiation of the transcription (e. g., translation initiation codon, promoters, enhancers, and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions. Preferably, the nucleic acid molecule of the invention is operatively linked to such expression control sequences allowing its expression. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the polynucleotide of the invention. Such leader sequences are well known in the art.

Possible examples for regulatory elements ensuring the initiation of transcription comprise the cytomegalovirus (CMV) promoter, SV40-promoter, RSV-promoter (Rous sarcoma virus), the lacZ promoter, the gai10 promoter, human elongation factor 1α-promoter, CMV enhancer, CaM-kinase promoter, the *Autographa californica* multiple nuclear polyhedrosis virus (AcMNPV) polyhedral promoter or the SV40-enhancer. For the expression in prokaryotes, a multitude of promoters including, for example, the tac-lac-promoter, the lacUV5 or the trp promoter, has been described. Examples for further regulatory elements in prokaryotes and eukaryotic cells comprise transcription termination signals, such as SV40-poly-A site or the tk-poly-A site or the SV40, lacZ and AcMNPV polyhedral polyadenylation signals, downstream of the polynucleotide.

Furthermore, it is preferred that the vector of the invention comprises a selectable marker. Examples of selectable markers include neomycin, ampicillin, and hygromycin resistance and the like. Specifically-designed vectors allow the shuttling of DNA between different hosts, such as bacteria-fungal cells or bacteria-animal cells.

An expression vector according to this invention is capable of directing the replication, and the expression, of the nucleic acid molecule and encoded fusion protein of this invention. Suitable expression vectors which comprise the described regulatory elements are known in the art such as pGreenPuro (System Biosciences, Mountain View, Calif., USA), pRc/CMV, pcDNA1, pcDNA3 (In-Vitrogene, as used, inter alia in the appended examples), pSPORT1 (GIBCO BRL) or pGEMHE (Promega), or prokaryotic expression vectors, such as lambda gt11, pJOE, the pBR1-MCS-series.

The nucleic acid molecules of the invention as described herein above may be designed for direct introduction or for introduction via liposomes, phage vectors or viral vectors (e.g. adenoviral, retroviral) into the cell. Additionally, baculoviral systems or systems based on Vaccinia Virus or Semliki Forest Virus can be used as eukaryotic expression system for the nucleic acid molecules of the invention.

The present invention further relates to a host cell comprising the nucleic acid molecule or the vector of the invention.

Suitable prokaryotic hosts comprise e.g. bacteria of the species *Escherichia*, *Streptomyces*, *Salmonella* or *Bacillus*. Suitable eukaryotic host cells are e.g. yeasts such as *Saccharomyces cerevisiae*, *Pichia pastoris*, *Schizosaccharomyces pombe* or chicken cells, such as e.g. DT40 cells. Insect cells suitable for expression are e.g. *Drosophila* S2, *Drosophila* Kc, or *Spodoptera* Sf9 and Sf21 cells. Suitable zebrafish cell lines include, without being limiting, ZFL, SJD or ZF4.

Mammalian host cells that could be used include, human Hela, HEK293, HEK293T, H9 and Jurkat cells, mouse NIH3T3 and C127 cells, COS 1, COS 7 and CV1, quail QC1-3 cells, mouse L cells, mouse sarcoma cells, Bowes melanoma cells, human CAP or CAP-T cells and Chinese hamster ovary (CHO) cells. Also within the scope of the present invention are primary mammalian cells or cell lines. Primary cells are cells which are directly obtained from an organism. Suitable primary cells are, for example, mouse embryonic fibroblasts (MEF), mouse primary hepatocytes, cardiomyocytes and neuronal cells as well as mouse muscle stem cells (satellite cells), human dermal and pulmonary fibroblasts, human epithelial cells (nasal, tracheal, renal, placental, intestinal, bronchial epithelial cells), human secretory cells (from salivary, sebaceous and sweat glands), human endocrine cells (thyroid cells), human adipose cells, human smooth muscle cells, human skeletal muscle cells, and stable, immortalized cell lines derived thereof (for example hTERT or oncogene immortalized cells).

Appropriate culture media and conditions for the above described host cells are known in the art.

The host cell in accordance with this embodiment may for example be employed in methods for the amplification of vectors of the invention, for the production of the fusion protein of the invention or for the direct production of lentivirus particles, as described in more detail herein below.

The present invention further relates to a polypeptide encoded by the nucleic acid molecule of the invention.

For example the polypeptide of the present invention may have an overall amino acid sequence selected from the sequences represented in SEQ ID NO: 8 or SEQ ID NO: 10.

The present invention further relates to a method of producing the VSV-G fusion protein of the invention, the method comprising culturing the host cell of the invention under suitable conditions and isolating the produced VSV-G fusion protein.

Suitable conditions for culturing a prokaryotic or eukaryotic host are well known to the person skilled in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. E. coli can be cultured from 4 to about 37° C., the exact temperature or sequence of temperatures depends on the molecule to be over-expressed. In general, the skilled person is also aware that these conditions may have to be adapted to the needs of the host and the requirements of the protein expressed. In case an inducible promoter controls the nucleic acid of the invention in the vector present in the host cell, expression of the polypeptide can be induced by addition of an appropriate inducing agent. Suitable expression protocols and strategies are known to the skilled person.

Depending on the cell type and its specific requirements, mammalian cell culture can e.g. be carried out in RPMI, Williams' E or DMEM medium containing 10% (v/v) FCS, 2 mM L-glutamine and 100 U/ml penicillin/streptomycine. The cells can be kept e.g. at 37° C. or at 41° C. for DT40 chicken cells, in a 5% CO2, water saturated atmosphere. Suitable media for insect cell culture is e.g. TNM+10% FCS or SF900 medium. Insect cells are usually grown at 27° C. as adhesion or suspension culture. Suitable expression protocols for eukaryotic or vertebrate cells are well known to the skilled person and can be retrieved e.g. from Sambrook and Russel, loc.cit.

The term "isolating" refers to a selective accumulation of the produced VSV-G fusion protein, by removing the produced VSV-G fusion protein from the host cells or from the medium in which the host cells have been cultured. Preferably, the isolated VSV-G fusion protein is 100% pure, i.e. is free of any other components that are not the VSV-G fusion protein of the invention. Methods of isolation of the fusion protein produced are well-known in the art and comprise, without limitation, method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook and Russel, loc. cit.

It will be appreciated by the skilled person that the term "isolation of the fusion protein produced" refers to the isolation of the protein encoded by the nucleic acid molecule of the present invention.

The present invention further relates to a lentiviral vector particle pseudotyped with (a) a VSV-G fusion protein domain encoded by the nucleic acid molecule of the invention; and (b) a VSV-G not linked to a (poly)peptide comprising or consisting of a cell membrane-binding domain.

A "lentiviral vector particle", also referred to herein as a "lentiviral vector", is a vector based on a lentivirus virion, i.e. a subclass of retroviruses that can integrate into the genome of non-dividing target cells. A unique feature of lentiviruses is that they have a self inactivated (SIN) region of replication in contrast to other retroviral vectors. Lentiviruses are well known in the art and have been described in detail, e.g., in Retroviruses, Coffin J M, Hughes S H, Varmus H E, Cold Spring Harbor (N.Y.): Cold Spring Harbour Laboratory Press; 1997; ISBN-10:0-87969-571-4; O'Connell R M, Balazs A B, Rao D S, Kivork C, Yang L, Baltimore D. Lentiviral vector delivery of human interleukin-7 (hIL-7) to human immune system (HIS) mice expands T lymphocyte populations. PLoS One. 2010 Aug. 6; 5(8): e12009; Mátrai J, Chuah M K, VandenDriessche T. Recent advances in lentiviral vector development and applications. Mol Ther. 2010 March; 18(3):477-90.

A lentiviral vector particle can be based, e.g., on a lentivirus of the group of bovine, equine, feline, ovine/caprine or primate lentiviruses. Preferably, the lentiviral vector is based on a primate lentivirus such as, HIV1, HIV2 or SIV virus. Most preferred, the lentiviral vector is based on an HIV1 lentivirus. As the skilled person is aware, most (commercially available) lentiviral vectors represent a mixture of viral constituents from different viruses and are, hence, to some extent "hybrid" vectors. For example, a lentiviral vector may comprise constituents from HIV1, VSVg, CMV, WPRE viruses. Such hybrid vectors are explicitly envisaged in accordance with the present invention.

The term "pseudotyped", as used herein in the context of viral vectors, refers to the modulation of the cell type specificity of a viral vector by integration of foreign viral envelope proteins. This approach is well known in the art and has been described for example in Bischof et al. (Flexibility in cell targeting by pseudotyping lentiviral vectors. Methods Mol Biol. 2010; 614:53-68). Using this approach, host tropism can be altered and/or the stability of the virus can be decreased or increased. For example, the use of VSV-G for pseudotyping a lentiviral virus has been described, e.g., in Burns et al. (Vesicular stomatitis virus G glycoprotein pseudotyped retroviral vectors: concentration to very high titer and efficient gene transfer into mammalian and nonmammalian cells. Proc Natl Acad Sci USA. 1993; 90(17): 8033-8037).

The term "a VSV-G not linked to a (poly)peptide comprising or consisting of a cell membrane-binding domain" is also referred to herein as wild type VSV-G. In this context, the term "wild type" only refers to the fact that no cell membrane-binding domain is fused to the VSV-G employed. However, the use of non-naturally occurring (i.e. modified)

VSV-G molecules is not excluded, as long as they are not linked to a (poly)peptide comprising or consisting of a cell membrane-binding domain.

As used herein, the terms "a VSV-G fusion protein" and "a VSV-G not linked to . . . " are not limited to "one" of the recited molecules. Instead, these terms define the types of molecules to be present, without any particular limitation in number. In other words, the term "a VSV-G fusion protein" explicitly encompasses one or more VSV-G fusion proteins and the term "a VSV-G not linked to . . . " explicitly encompasses one or more VSV-Gs not linked to a (poly) peptide comprising or consisting of a cell membrane-binding domain.

In accordance with the present invention, a lentivirus vector particle is provided that is pseudotyped with two different types of VSV-G proteins, namely with the fusion protein of the invention described herein above (option (a)) and with a VSV-G that has not been fused to a cell membrane-binding domain, i.e. a wild-type (wt) VSV-G (option (b)). In other words, each individual lentivirus vector particle expresses both modified and wild type VSV-G glycoproteins on its surface.

In accordance with the present invention, it was surprisingly found that pseudotyping with both these VSV-Gs is advantageous over the use of one of these proteins alone. First, the use of 100% of the VSV-G fusion protein of the invention failed to infect cells in cytometric assays, as shown e.g. in Example 4, thus not achieving the intended transduction. Second, as is also shown in the appended examples, a mixture of the inventive molecule with wt-molecules led to enhanced infection rates as compared to wild type alone.

In a preferred embodiment of the lentivirus vector particle of the invention, the ratio of (a):(b) exhibited by said pseudotyped lentiviral vector particle in the viral envelope is between 10%:90% and 50%:50%.

In other words, in accordance with this preferred embodiment, the ratio of VSV-G fusion protein of the invention to wt-VSV-G is in the range between about 10% VSV-G fusion protein of the invention to about 90% wt-VSV-G and about 50% VSV-G fusion protein of the invention to about 50% wt-VSV-G. Preferably, the ratio is about 33% of the VSV-G fusion protein of the invention and about 67% wt-VSV-G.

The term "about", as used herein, encompasses the explicitly recited values as well as small deviations therefrom. In other words, a percentage of "about 33%" includes, but does not have to be exactly the recited amount of 33% but may differ by several %, thus including for example 31%, 32%, 34%, or 35%. The skilled person is aware that such values are relative values that do not require a complete accuracy as long as the values approximately correspond to the recited values. Accordingly, a deviation from the recited value of for example 15%, more preferably of 10%, and most preferably of 5% is encompassed by the term "about".

The present invention further relates to a method of producing the pseudotyped lentiviral vector particle of the invention, the method comprising transfecting into a host cell (i) one or more packaging plasmids encoding the virion proteins and accessory proteins needed for efficient production and packaging of the LTR-containing nucleic acid; (ii) a vector comprising the nucleic acid molecule of the invention; and (iii) a vector comprising a nucleic acid molecule encoding a VSV-G not linked to a (poly)peptide comprising or consisting of a cell membrane-binding domain.

Such methods of producing pseudotyped lentiviral vectors are well known in the art and have been described, e.g. in Naldini, L. (1998) [61]. Host cells, preferably HEK 293, HEK293T, CAP or CAP-T cells are employed and a number of vectors, including the packaging vector(s) encoding the viral proteins, such as e.g. the capsid and the reverse transcriptase, as well as vectors carrying the nucleic acid molecules to be additionally introduced into the pseudotyped lentiviral vector particle are transfected or electroporated into these cells, or nucleofection is used to transfer said vectors. In addition, further vectors containing the genetic material to be delivered by the pseudotyped lentiviral vector particle may be transfected.

These vectors may be introduced into the host cells by direct introduction or by introduction via electroporation (using for example Multiporator (Eppendorf), Genepulser (BioRad), MaxCyte Transfection Systems (Maxcyte)), PEI (Polysciences Inc. Warrington, Eppelheim), Ca2+-mediated transfection or via liposomes (for example: "Lipofectamine" (Invitrogen)), non-liposomal compounds (for example: "Fugene" (Roche) or nucleofection (Lonza)) into cells.

All of the definitions and preferred embodiments provided herein above with regard to the pseudotyped lentiviral vector particle of the invention apply mutatis mutandis to the method for producing the pseudotyped lentiviral vector particle of the invention. For example, the preferred ratios between the VSV-G fusion protein of the invention and a VSV-G that is not fused to a cell membrane-binding domain apply equally to the ratios employed in the production process of the pseudotyped lentiviral vector particles of the invention. Thus, in order to obtain e.g. the preferred ratio of about 67% of the VSV-Gs not linked to a (poly)peptide comprising or consisting of a cell membrane-binding domain to about 33% of the VSV-G fusion protein of the invention 33%, twice as much of the vector of option (iii) is added to the host cells as compared to the vector of option (ii), thus resulting in an approximate 2:1 ratio, i.e. 67% to 33%.

The present invention further relates to a method for transducing cells, the method comprising the step of: contacting cells to be transduced with the pseudotyped lentiviral vector particle of the invention under conditions suitable for transduction, thereby transducing said cells. Accordingly, the present invention also relates to the use of lentiviral vector particles of the invention for the transduction of target cells.

The term "transducing", as used herein, is well known in the art and refers to the process of introducing genetic material into a cell and, optionally, its subsequent integration into the genome of said cell via viral vector particles. Said genetic material comprises or consists of viral RNA combined with one or more target RNA sequences (hereinafter referred to as target sequences) comprised in said viral vector particles intended for integration into the genome of a target cell.

The term "contacting" as used herein in the context of this method of the invention refers to bringing the cells to be transduced (also referred to herein as "target cells") into contact with a retroviral vector so that the transduction event can occur. Conditions for contacting that allow the transduction event to occur are well known in the art and may depend to a certain extent on the cell to be transduced. For example, some target cells are more difficult to transfect than other cells and may need to be transitioned into a specific culture medium before transduction with a viral vector can be achieved. Corresponding methods and conditions are described for example in Jacome et al. (Lentiviral-mediated Genetic Correction of Hematopoietic and Mesenchymal Progenitor Cells From Fanconi Anemia Patients. Mol Ther. 2009 June; 17(6): 1083-1092), Chu et al. (Efficient and Stable Gene Expression into Human Osteoclasts Using an HIV-1—Based Lentiviral Vector. DNA Cell Biol. 2008 June; 27(6): 315-320), or Poczobutt et al. (Benign mammary epithelial cells enhance the transformed phenotype of human breast cancer cells. BMC Cancer. 2010; 10: 373). Exemplary conditions are described in the example section.

In accordance with the present invention, the cells to be transduced can be any cells of interest that are to be targeted for transduction with a viral vector. The term "cell/cells" as used in connection with the present invention can refer to single and/or isolated cells or to cells that are part of a multicellular entity such as a tissue, an organism or a cell culture. In other words the method can be performed in vivo, ex vivo or in vitro. Preferably, the cells to be transduced are eukaryotic cells including any cell of a multi-cellular eukaryotic organism, preferably cells from animals like vertebrates. More preferably, the cells to be transduced are mammalian cell. Depending on the particular goal to be achieved through modifying the genome of a mammalian cell by transducing it according to the method of the invention, cells of different mammalian subclasses such as prototheria or theria may be used. For example, within the subclass of theria, preferably cells of animals of the infraclass eutheria, more preferably of the order primates, artiodactyla, perissodactyla, rodentia and lagomorpha are used in the method of the invention. Furthermore, within a species one may choose a cell to be used in the method of the invention based on the tissue type and/or capacity to differentiate equally depending on the goal to be achieved by modifying the genome via transducing a target cell according to the method of the invention. Three basic categories of cells, which in principle can be transduced with the method of the invention, make up the mammalian body: germ cells, somatic cells and stem cells. A germ cell is a cell that gives rise to gametes and thus is continuous through the generations. Stem cells can divide and differentiate into diverse specialized cell types as well as self renew to produce more stem cells. In mammals there are two main types of stem cells: embryonic stem cells and adult stem cells. Somatic cells include all cells that are not a gametes, gametocytes or undifferentiated stem cells. The cells of a mammal can also be grouped by their ability to differentiate. A totipotent (also known as omnipotent) cell is a cell that is able to differentiate into all cell types of an adult organism including placental tissue such as a zygote (fertilized oocyte) and subsequent blastomeres, whereas pluripotent cells, such as embryonic stem cells, cannot contribute to extraembryonic tissue such as the placenta, but have the potential to differentiate into any of the three germ layers endoderm, mesoderm and ectoderm. Multipotent progenitor cells have the potential to give rise to cells from multiple, but limited number of cell lineages. Further, there are oligopotent cells that can develop into only a few cell types and unipotent cells (also sometimes termed a precursor cell) that can develop into only one cell type. There are four basic types of tissues: muscle tissue, nervous tissue, connective tissue and epithelial tissue that cells to be used in the method of the invention can be derived from, such as for example lymphoid lineage cells or neuronal stem cells. To the extent human cells are envisaged for use in the method of the invention, it is preferred that such human cell is not obtained from a human embryo, in particular not via methods entailing destruction of a human embryo. On the other hand, human embryonic stem cells are at the skilled person's disposal such as taken from existent embryonic stem cell lines commercially available or obtained by methods that do not require the destruction of a human embryo. Alternatively, or instead of human embryonic stem cells, pluripotent cells that resemble embryonic stem cells such induced pluripotent stem (iPS) cells may be used, the generation of which is state of the art (Hargus G et al., 2010, Proc Natl Acad Sci USA, 107:15921-15926; Jaenisch R. and Young R., 2008, Cell 132:567-582; Saha K, and Jaenisch R., 2009, Cell Stem Cell 5:584-595).

As discussed herein above and as shown in the appended examples, it was found in accordance with the present invention that even difficult to transduce cells such as lymphoma cell lines or tumor cell lines can be transduced by a method employing the lentiviral vector particles of the present invention.

In a preferred embodiment of the method for transducing cells of the present invention, the method further comprises contacting the cells with an adjuvant, preferably a poloxamer having a molecular weight of 12.8 kDa to about 15 kDa.

The term "adjuvant", as used herein, relates to a compound that enhances the efficiency of the lentiviral transduction. Non-limiting examples of adjuvants include e.g. a poloxamer having a molecular weight of 12.8 kDa to about 15 kDa and polybrene.

Preferably, the method for transducing cells of the present invention further comprises contacting the cells with a poloxamer having a molecular weight of 12.8 kDa to about 15 kDa.

The term "poloxamer" is well known in the art and refers to a non-ionic triblock copolymer composed of a central hydrophobic chain of polyoxypropylene flanked by two hydrophilic chains of polyoxyethylene. The block copolymer can be represented by the following formula:

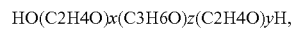

HO(C2H4O)x(C3H6O)z(C2H4O)yH, wherein z is an integer such that the hydrophobic base represented by (C3H6O) has a molecular weight of at least 2250 Da and x or y is an integer from about 8 to 180 or higher. Poloxamers are also known by the trade name of "Pluronics" or "Synperonics" (BASF). The lengths of the polymer blocks can be customized; as a result many different poloxamers exist. A poloxamer to be used in accordance with the method of the invention is a poloxamer having a molecular weight of at least 12.8 kDa to about 15 kDa. As evident from the above general formula, poloxamers having a corresponding molecular weight can be composed by changing the length of the polymer blocks making up a poloxamer. For example, two poloxamers can have about the same molecular weight but are structurally different, because one poloxamer may have more repetitions of the hydrophobic block polymer and less repetitions of the hydrophilic block polymer while the other poloxamer has more repetitions of the hydrophilic block polymers and less repetitions of the hydrophobic block polymer. For example, z can be in the range of 42 to 52, such as at least (for each value) 43, 44, 45, 46, 47, 48, 49, 50 or at least 52; and x+y can be in the range of 220 to 360, such as at least (for each value) 230, 240, 250, 260, 270, 280, 290, 300, 310, 320, 330, 340, or at least 350. Preferably, z is in the range of 44 to 50 and x+y is in the range of 235 to 266. As synthesis of block copolymers cannot be accurate, the above given values may not exactly be achievable upon synthesis and the average value will differ to a certain extent (as described herein). Preferably, the poloxamer has a molecular weight of 12.8 to about 14.9 kDa, of about 13.2 to about 14.9 kDa, of about 13.4 to about 14.9 kDa, or more preferred of about 14.0 to about 14.9 kDa, of about 14.3 to about 14.8 kDa, of about 14.5 to about 14.7 kDa, and most preferred of about 14.6 kDa. As understood by the person skilled in the art, the method can be performed using a multitude of poloxamers.

Thus, the term "poloxamer" as used herein can be used interchangeably with the term "poloxamers" (representing an entity of several poloxamers, also referred to as mixture of poloxamers) if not explicitly stated otherwise. As outlined herein, synthesis of poloxamers is inaccurate resulting in a mixture of poloxamers with varying molecular weight. Thus, the term "average" in relation to molecular weight of (a) poloxamer(s) as used herein is a consequence of the technical inability to produce poloxamers all having the identical composition and thus the identical molecular weight. Thus, poloxamers produced according to state of the art methods will be present as a mixture of poloxamers each showing a variability as regards their molecular weight, but the mixture as a whole averaging the molecular weight specified herein. The person skilled in the art is in the position to obtain poloxamers that can be used in the method of the invention. For example, BASF and Sigma Aldrich provide poloxamers as defined herein. Methods for determining the molecular weight are well known in the art and described in standard textbooks of chemistry. Experimentally, high pressure liquid chromatography (HPLC) can be used to determine the molecular weight of a poloxamer.

The lentiviral vector particles and the adjuvant, preferably the poloxamer, can be added simultaneously, e.g. as a mixture, to the target cells or in sequential mode, as long as both compounds are simultaneously in contact with the target cell to allow transduction. Preferably, the target cell, lentiviral vector particles and adjuvant (poloxamer) are contacted for at least 5 hours, such as at least 6, at least 7, at least 8, more preferred at least 9, at least 10, at least 11, and most preferred at least 12 hours. Also envisaged are longer contacting times such as at least 13, at least 14, at least 15, at least 16, or at least 24 hours. Preferred is the simultaneous addition of the lentiviral vector particles and the adjuvant, preferably the poloxamer.

The use of poloxamers as defined herein above has been found previously (WO2013/127964) to significantly enhance the transduction efficiency of retroviral vectors in adherent and suspension target cells without essentially affecting their viability. Briefly, using lentiviral vectors it could be shown that the poloxamer designated "symperonic F108" (HO—[CH2CH2O]x-[CH2C2H4O]z-[CH2CH2O]y with x+y=265.45 and z=50.34 (Kabanov, A., Zhu, J. & Alakhov, V. Adv. Genet. 53, 231-261 (2005)); average molecular weight: 14.6 kDa) showed less cytotoxicity than the state of the art transduction enhancer polybrene (1,5-dimethyl-1,5-diaza-undeca-methyl-polymethobromide) even at concentrations 100 times higher than those of polybrene and enhanced transduction efficiency (HEK293T cells). Most surprisingly, the transduction enhancing effect of the poloxamer used was not confined to specific cell types. Whereas many established tumor cell lines have been difficult to infect, it could be shown in WO2013/127964 that use of synperonic F108 (average molecular weight of 14.6 kDa consisting of 265 hydrophilic ethylene oxide (EO) units and 50 hydrophobic propylene oxide (PO) units; further defined below) greatly increased infection rates of hard-to-transfect lymphoma cell lines.

In a preferred embodiment of the method of the invention, the poloxamer has the formula HO—[CH2CH2O]x-[CH2C2H4O]z-[CH2CH2O]y, wherein x+y=265.45 and z=50.34 on average (synperonic F108); or the poloxamer has the formula

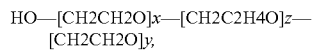

wherein x+y=236.36 and z=44.83 on average (F98).

The poloxamer of the first formula is known in the art as synperonic F108 and is synthesized as a white granulate with an average molecular weight of 14.6 kDa consisting of about 265 hydrophilic ethylene oxide (EO) units and about 50 hydrophobic propylene oxide (PO) units. Block copolymers are synthesized by sequential addition of PO and EO monomers in the presence of an alkaline catalyst, initiated by polymerization of the PO block followed by the growth of EO chains at both ends of the PO block. As synthesis of block copolymers cannot be exact, the repetitions of x+y and z are given as averages. Accordingly, and with regard to the term "on average" the above given definition of synperonic F108 includes poloxamers deviating from said median, i.e. it includes poloxamers falling within the standard deviation from the mean (average). This ratio accounts for its particularly unproblematic solubility in water or phosphate buffer (Kabanov, A., Zhu, J. & Alakhov, V. Adv. Genet. 53, 231-261 (2005)). In aqueous solution, single poloxamer molecules called unimers are described to self-assemble as micelles with a PO core and an EO shell. Synperonic F108 as an exemplary poloxamer having a molecular weight within the range defined herein has been shown in WO2013/127964 to act as a potent enhancer of transduction efficiency on target cells, particularly target cells that are known to be difficult to transfect.

The poloxamer of the second formula is known in the art as F98 (Kabanov, A et al. Advances in Genetics. 2005; 53: 231-261.) and is—as synperonic F108—preferably used in accordance with the invention. The definition as regards the term "on average" given for synperonic F108 applies also to F98.

In a preferred embodiment of the method of the invention, said poloxamer is provided at a concentration of about 50 to 5000 μg/ml.

The term "about" as defined herein above, mutatis mutandis applies to this embodiment.

Particularly preferred is a concentration of about 100 to 4000 μg/ml, more preferably about 200 to 3000 μg/ml, even more preferably about 300 to 2000 μg/ml, even more preferably about 400 to 1500 μg/ml and most preferably about 450 to 1250 μg/ml. Also preferred are concentrations of about 600 to 1000 μg/ml, 700 to 1000 μg/ml, 800 to 1000 μg/ml, or 900 to 1000 μg/ml. At the latter concentrations, poloxamers as defined herein are in a fluid state when diluted in water or phosphate buffer. As will be understood by the skilled person, transducing cells with fluid poloxamers may be practically more convenient as, e.g., it allows convenient handling such as easier pipetting.

In accordance with this method of the invention, the poloxamers are preferably dissolved in water, phosphate buffer or directly in cell culture medium. Poloxamers can be dissolved, e.g., in water or phosphate buffer to obtain 100 mg/ml stock solutions that can be diluted to a given working concentration. At concentrations of more than 200 mg/ml poloxamer solutions are gel-like. At concentrations below 200 mg/ml poloxamer solutions are in a fluid state. Preferably, the concentrations are such that the poloxamer is provided in a fluid state.

In a further preferred embodiment of the method of the invention, the target cells are further brought into contact with one or more polycationic substances selected from the group of polycationic polymers or polycationic peptides.

"Polycationic polymers" in accordance with the present invention refers to charged polymers whose repeating units bear a positive charge, wherein the positive charge on a repeating unit stems from protonated nitrogen moieties. For example, in polyethylenimine (PEI) the positively charged group is the imine group. Another non-limiting example of a polycationic polymer is the substance polybrene (5-dimethyl-1,5-diazaundecamethylene polymethobromide, hexadimethrine bromide).

The term "polycationic peptides" refers to positively charged peptides. For example, poly-L-lysine is a homopolymeric polycationic peptide with the molecular formula of (C6H12N2O)n, wherein in accordance with the invention, but without limitation, n may be at least 2, such as at least 20, preferably between 200 and 500, more preferred between 500 and 2500.

In a further preferred embodiment of the method of transducing cells of the invention, the method comprises a further step of spinoculating the pseudotyped lentiviral vector particle with the cells prior to, concomitant with or after contacting said target cell with said adjuvant.

In a further more preferred embodiment of the method of transducing cells of the invention, the method comprises a further step of spinoculating the pseudotyped lentiviral vector particle with the cells prior to, concomitant with or after contacting said target cell with said poloxamer.

The term "spinoculating" is well known in the art and relates to centrifugal inoculation of target cells with the lentiviral vector particles to ensure close contact for cellular uptake of the virus particles. Spinoculation protocols are well known in the art and have been described for example for lentiviral vectors in Millington et al., 2009 [44]. A spinoculation step can be executed prior to, concomitant with or after contacting the target cells with said adjuvant, preferably said poloxamer. Preferably, the spinoculation step is performed after contacting the target cells with the adjuvant, preferably said poloxamer.

The spinoculation step further increases transduction rates achieved with the method of the invention, particularly in cells that are difficult to transfect, as shown in Example 5.

In a further preferred embodiment of the method of transducing cells of the invention, the cells to be transduced are selected from the group consisting of tumour cells, lymphoid lineage cells, epithelial cells, neuronal cells and stem cells and/or, preferably, wherein the cells to be transduced are part of a heterogeneous cell population.

The term "tumor cell" in accordance with the invention is well known in the art and refers to a neoplastic cell involved in the formation of benign, premalignant or malignant tumors. Tumor cells that are malignant are generally referred to as cancer cells and may have the ability to metastasize or spread to neighbouring tissue. Preferred tumor cells, are e. g., pancreatic tumor cells (such as, e.g., AsPC-1 and PANC-1 cells), lymphoma cell lines (such as, e.g., KARPAS-299, SUDHL-1, SUP-M2 and SR-786 cells) and breast cancer cells (such as, e.g., MCF7, MDA-MB-361 and T47D cells).

The term "lymphoid lineage cells" refers to cells that are involved in the generation of lymphocytes and lymphocytes per se. The term "lymphocyte" refers to small lymphocytes (B and T lymphocytes, plasma cells) and natural killer cells as well-known in the art. Lymphoid lineage cells further include, e.g., lymphoid dendritic cells, as well as lymphocyte progenitor cells such as pro-lymphocytes, lymphoblasts, common lymphoid progenitor cells.

The term "epithelial cell" is well known in the art. Epithelial cells line cavities and surfaces of structures throughout the body and also form many glands. Epithelial tissues can be classified into simple epithelium (one cell thick) and stratified epithelium (several layers of cells). Epithelial cells are furthermore classified by their morphology into squamous, cuboidal, columnar and pseudostratified epithelial cells. For example, the human stomach and intestine is lined with epithelial cells. Further, epithelial cell lines include also breast carcinoma cells (such as, e.g., MCF7, MDA-MB-361 and T47D cells) or cells of the cell line HEK293T.

"Neuronal cells" are well-known in the art and are cells that are electrically excitable transmitting information by electrical and chemical signalling. Various specialized neuronal cells exist such as, e.g., sensory neurons and motor neurons. For example, basket cells, Betz cells, medium spiny neurons, Purkinje cells, pyramidal cells, Renshaw cells, granule cells or anterior horn cells can be used as target cells in accordance with the invention. A "neuronal tumor cell" is a tumor cell of neuronal origin, for example, Gliomas, Medulloblastoma, Astrocytoma and other cancers derived from neuronal lineage. Glioma cell lines (such as, e.g. U87 and LN18) can be used in the method of the invention.

The term "stem cell" is well-known in the art and has been detailed herein above. Preferred stem cells for use according to the method of the invention are, e.g., embryonic stem cells, induced pluripotent stem cells, hematopoietic stem cells, cancer stem cells.

All of these cell types are typically considered to be difficult to transfect or to transduce but can now be transduced more efficiently based on the method of the present invention.

In an additional, or preferred, embodiment, the cells to be transduced are part of a heterogenous cell population, i.e. a cell population comprising different types of cells (also referred to herein as "a mixed population"). As is shown in the appended examples, in particular in Example 4 and 6, transduction is specifically enhanced in cells carrying a target molecule to which the cell membrane-binding domain can bind. In mixed cell population containing cells with and without such a target molecule, the transduction equilibrium is shifted towards the cells carrying said target molecule. Thus, a gain of relative specificity of the retargeted lentiviral particles towards their target cells even in the presence of competing non-target cells has been shown herein.

The present invention further relates to a kit comprising:

(a)(i) a nucleic acid molecule of the invention; or (a)(ii) a nucleic acid molecule of the invention and a nucleic acid molecule comprising or consisting of a nucleic acid sequence encoding a VSV-G not linked to a (poly)peptide comprising or consisting of a cell membrane-binding domain;

and/or (b)(i) a vector of the invention; or (b)(ii) a vector of the invention and a vector comprising a nucleic acid molecule comprising or consisting of a nucleic acid sequence encoding a VSV-G not linked to a (poly)peptide comprising or consisting of a cell membrane-binding domain;

and/or (c)(i) a host cell of the invention; or (c)(ii) a host cell of the invention and host cell comprising a vector comprising a nucleic acid molecule comprising or consisting of a nucleic acid sequence encoding a VSV-G not linked to a (poly)peptide comprising or consisting of a cell membrane-binding domain;

and/or (d)(i) a polypeptide of the invention; or (d)(ii) a polypeptide of the invention and a VSV-G not linked to a (poly)peptide comprising or consisting of a cell membrane-binding domain;

and/or (e) a pseudotyped lentiviral vector particle of the invention; and, optionally, instructions for use.

The various components of the kit may be packaged in one or more containers such as one or more vials. The vials may, in addition to the components, comprise preservatives or buffers for storage, media for maintenance and storage, e.g. ES cell media, DMEM, MEM, HBSS, PBS, HEPES, hygromycin, puromycin, Penicillin-Streptomycin solution, gentamicin inter alia. Advantageously, the kit comprises instructions for use of the components allowing the skilled person to conveniently work, e.g., various embodiments of the invention. Any of the components may be employed in an experimental setting.

The definitions and preferred embodiments described herein above with regard to the nucleic acid molecule of the invention, the vector of the invention, the host cell of the invention, the polypeptide of the invention or the pseudotyped lentiviral vector particle of the invention apply mutatis mutandis to the components of the kit of the invention. For example, the pseudotyped lentiviral vector particle of the invention can be combined with a poloxamer, as described herein above. To give another example, the preferred ratios between the VSV-G fusion protein of the invention and a VSV-G that is not linked to a cell membrane-binding domain apply equally to the ratios for the components of the kit in accordance with option (a)(ii). Thus, it is particularly preferred to include in the kit a nucleic acid molecule of the invention in an amount of 33% of the total amount of VSV-G and a nucleic acid molecule comprising or consisting of a nucleic acid sequence encoding a VSV-G not linked to a (poly)peptide comprising or consisting of a cell membrane-binding domain in an amount of 67% of the total amount of VSV-G.

Unless otherwise defined, all technical and scientific terms used herein have the same meaning as commonly understood by one of ordinary skill in the art to which this invention belongs. In case of conflict, the patent specification, including definitions, will prevail.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims.

The figures show:

FIG. 1: Design and production of lentiviral particles containing scFv-VSV-G fusions. VSV-G Plasmids used for wild type (wt) and scFv-added lentivirus production: To gain CD30 or EGFR specificity, a scFv antibody fragment against either antigen was cloned between the signal sequence (SS) and the protein sequence of VSV-G. For detection purposes, a His-tag was fused to the N-terminus. Abbreviations: VSV-G—envelope glycoprotein G of vesicular stomatitis virus; His6—His-tag consisting of six histidine residues; VH/VL—variable heavy/light chain.

Figure 2:
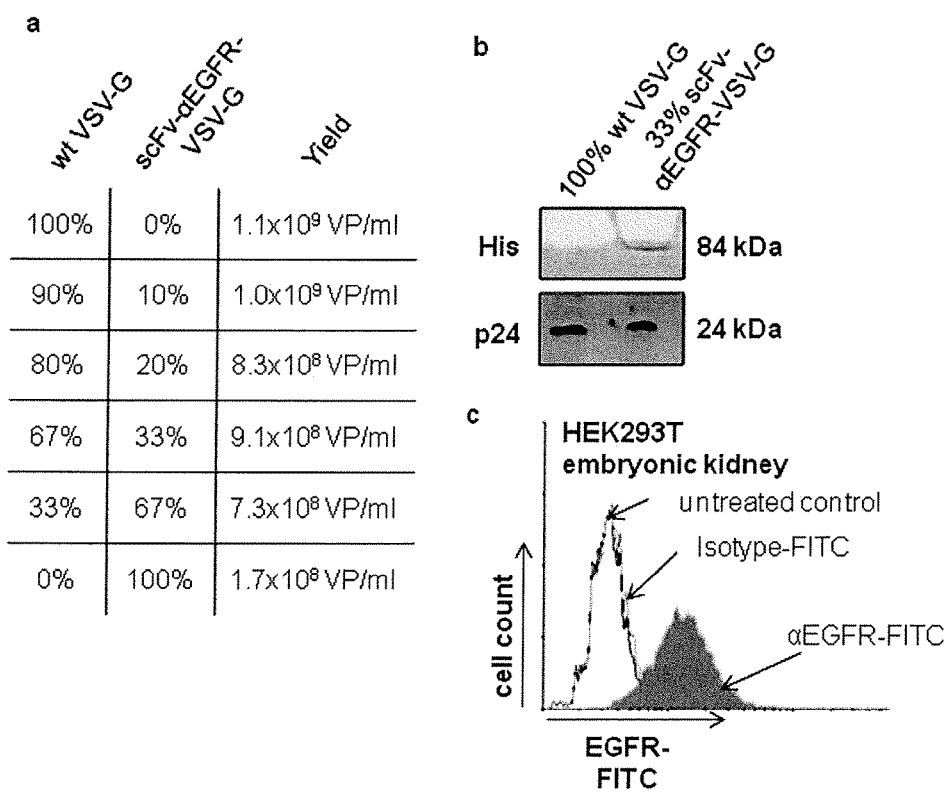
Figure 2:
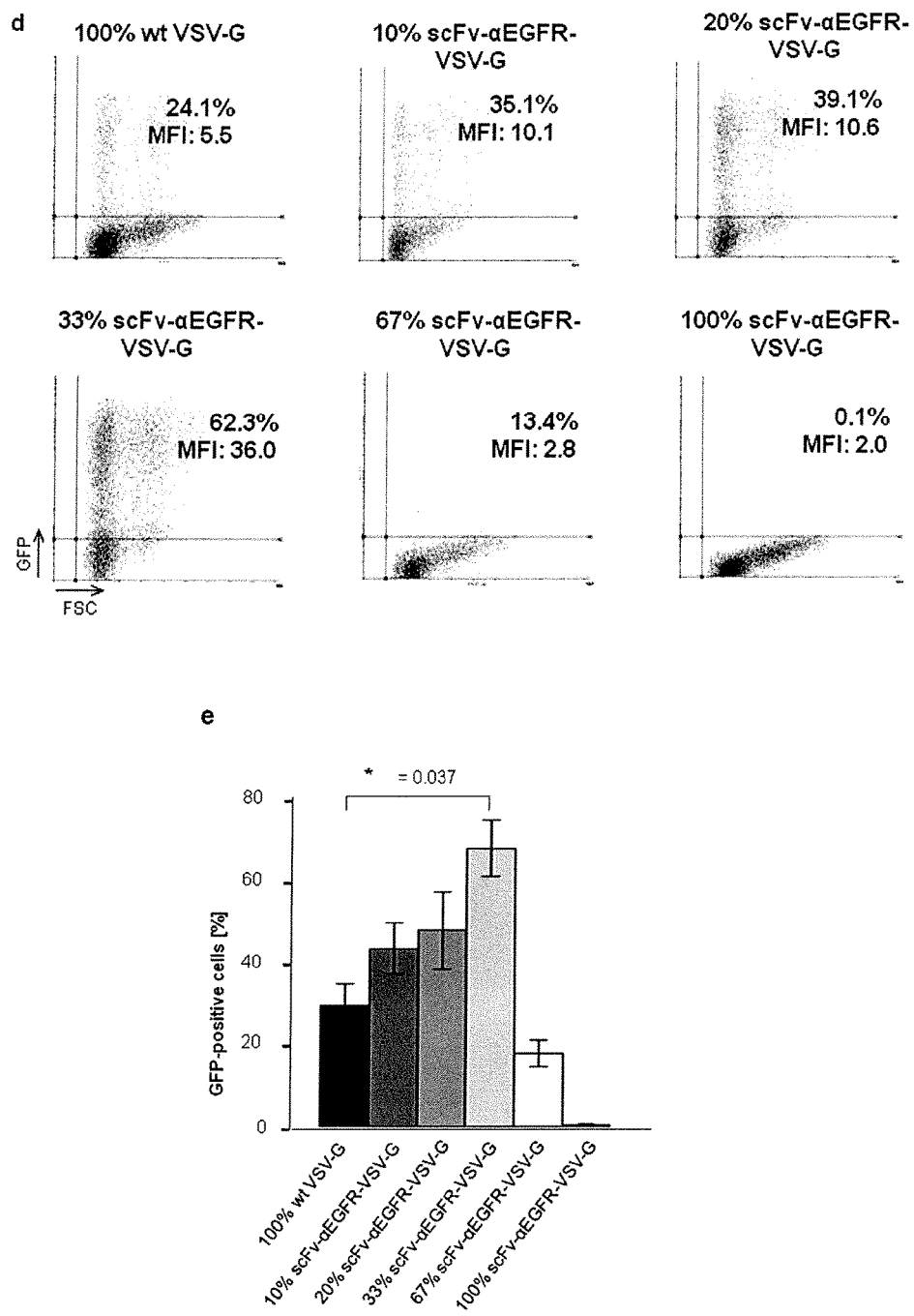

FIG. 2: Transduction of EGFR+ HEK293T cells with different ratios of scFv-αEGFR-added lentiviral particles. (a) Yields of six different copGFP-coding lentiviral particles that were produced using different ratios of packaging plasmids encoding wt VSV-G and scFv-αEGFR-VSV-G. (b) Immunoblotting assay of antibody-retargeted lentiviral particles (33% scFv-αEGFR-VSV-G, right lane) via His-tag (84 kDa). 100% wt VSV-G lentiviral particles (left lane) and lentiviral p24 core protein (24 kDa) served as reference. (c) FACS analysis of EGFR-expression on surface of HEK293T cells. (d) FACS analysis of GFP-expression in HEK293T cells transduced with different ratios (as in a) of scFv-added lentiviral particles at MOI 1 (MFI—median fluorescence intensity). (e) Statistical quantification of transduction experiments in HEK293T cells performed as described in (d) (three different experiments, mean±SD, $*p<0.05$, by t-test).

Figure 3:
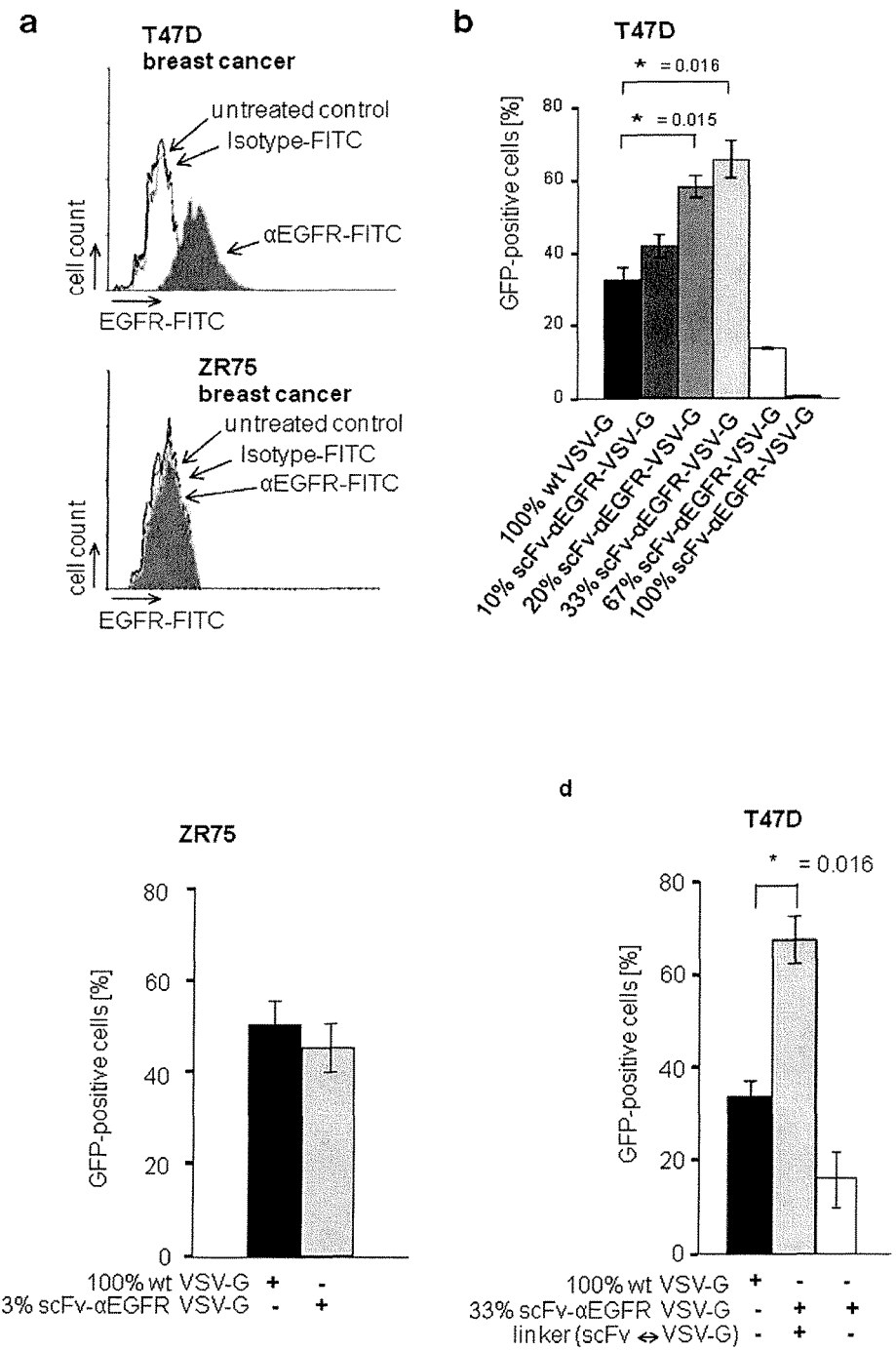

FIG. 3: Factors that affect antibody-retargeted lentiviral transduction. (a) FACS analysis of EGFR-expression on surface of T47D (EGFR+) and ZR75 (EGFR−) cells. (b+c) Quantification of GFP-expression after transduction of T47D (b) and ZR75 (c) cells with different ratio types of copGFP-coding scFv-added lentiviral particles at MOI 1. (d) Quantification of transduction experiments in T47D cells incubated with wt and scFv-αEGFR-added lentiviral particles (MOI 1) carrying a fusion linker between the scFv antibody fragment and VSV-G or not carrying such a fusion linker (three different experiments, mean±SD, $*p<0.05$, by t-test).

Figure 4:
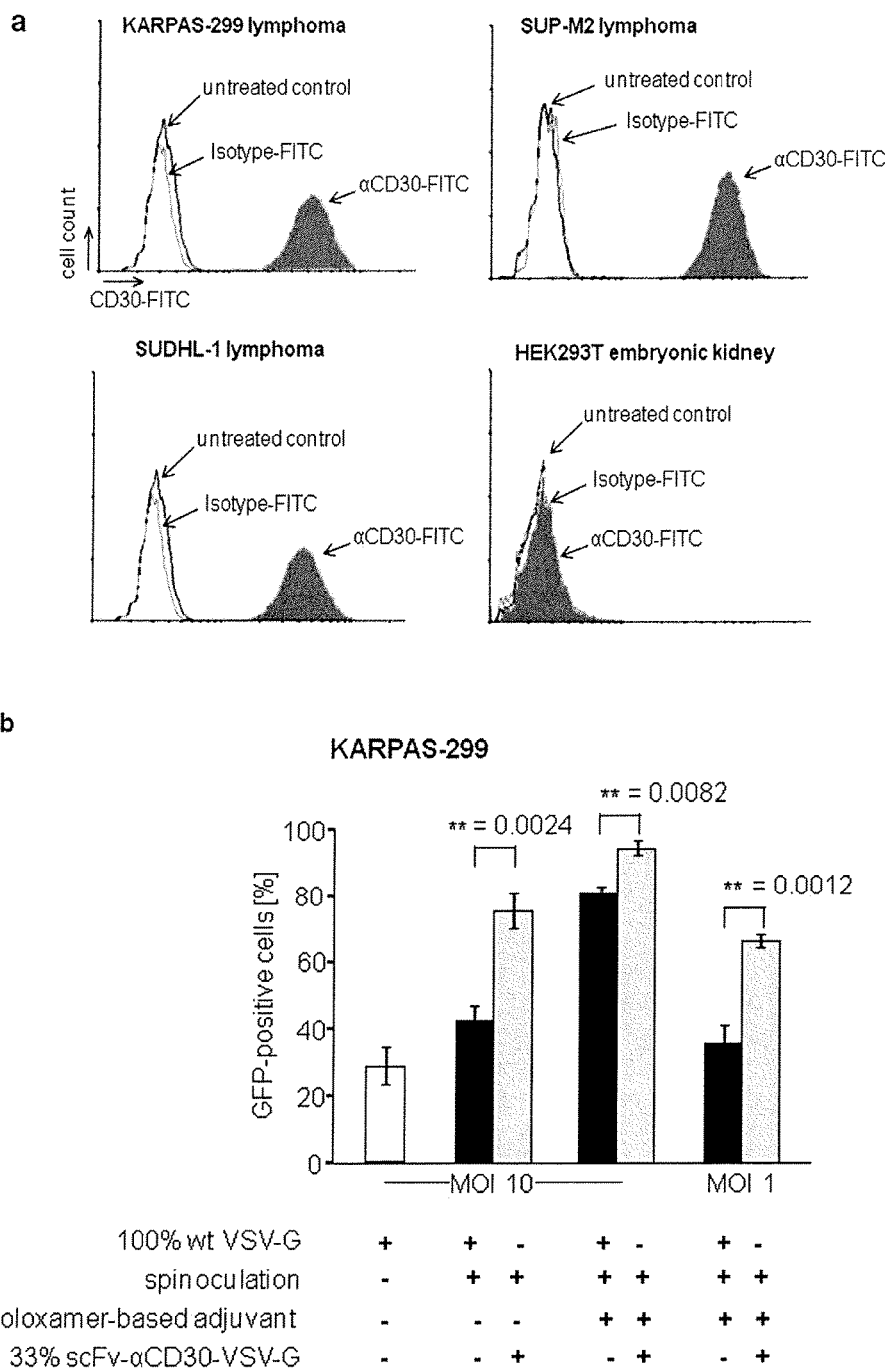
Figure 4:
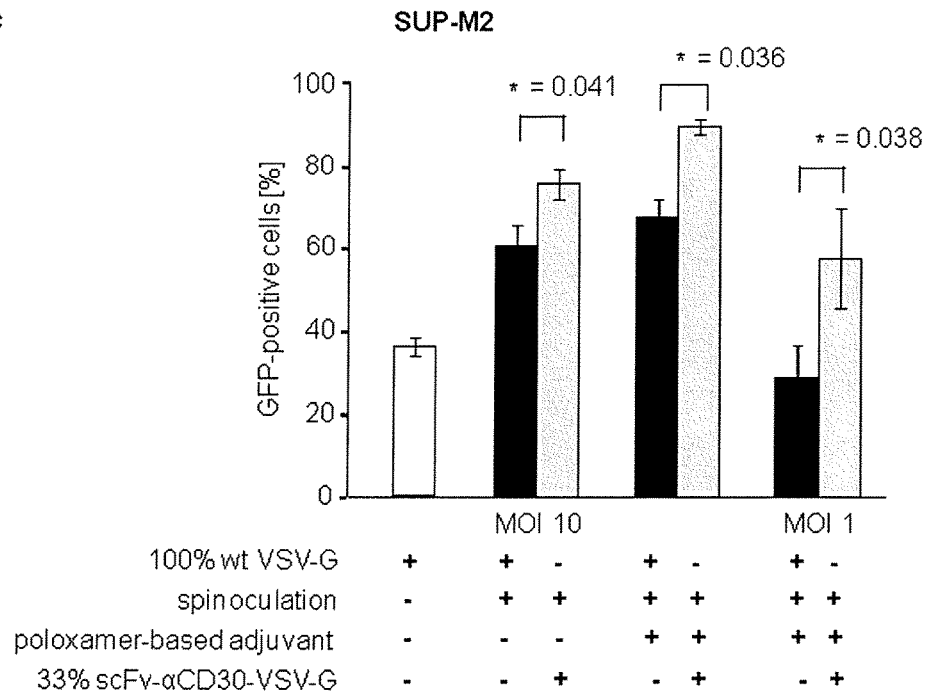
Figure 4:
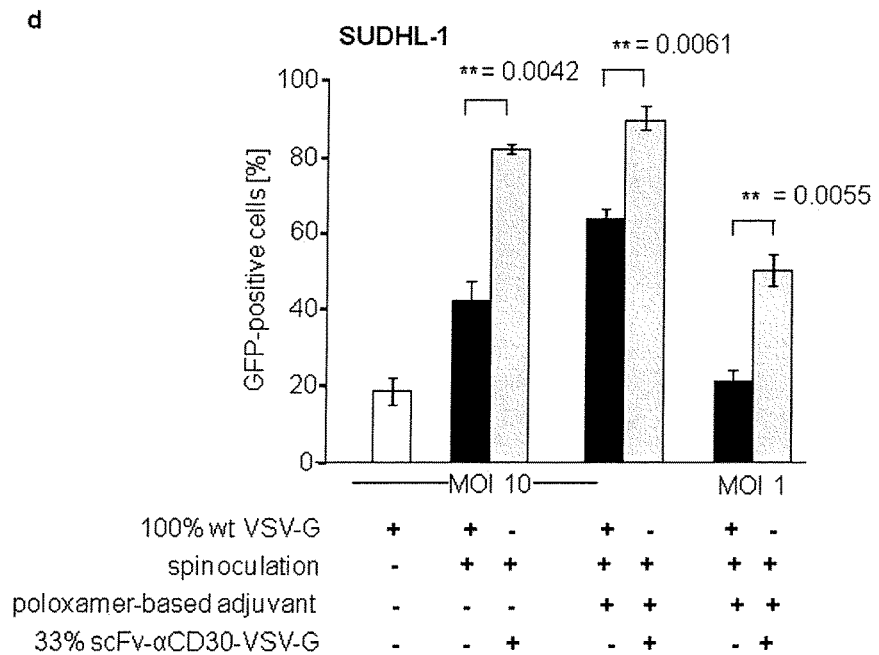
Figure 4:
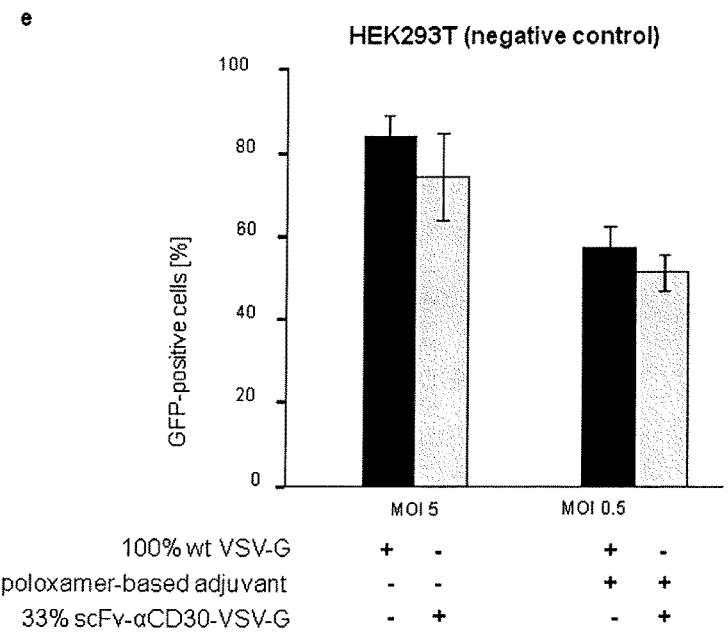

FIG. 4: Transduction of CD30+ lymphoma cells with scFv-αCD30-added lentiviral particles. (a) FACS analysis of CD30-expression on surface of KARPAS-299, SUP-M2, SUDHL1 and HEK293T cells. (b-e) Quantification of transduction experiments in described cells incubated with MOI 10 and 1 of copGFP-coding lentiviral particles with or without spinoculation, poloxamer-based adjuvant and scFv-αCD30-added VSV-G (three different experiments, mean±SD, $*p<0.05$, $**p<0.01$ by t-test).

Figure 5:
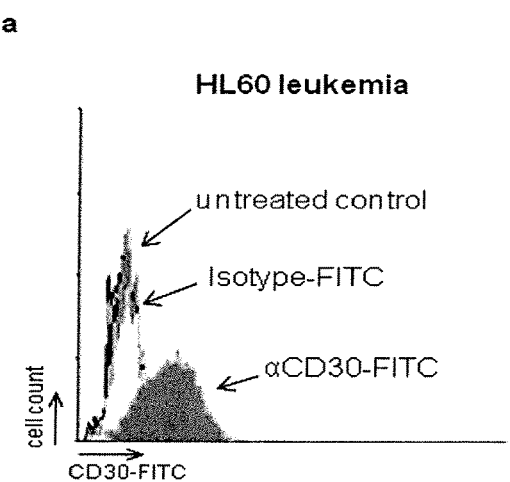
Figure 5:
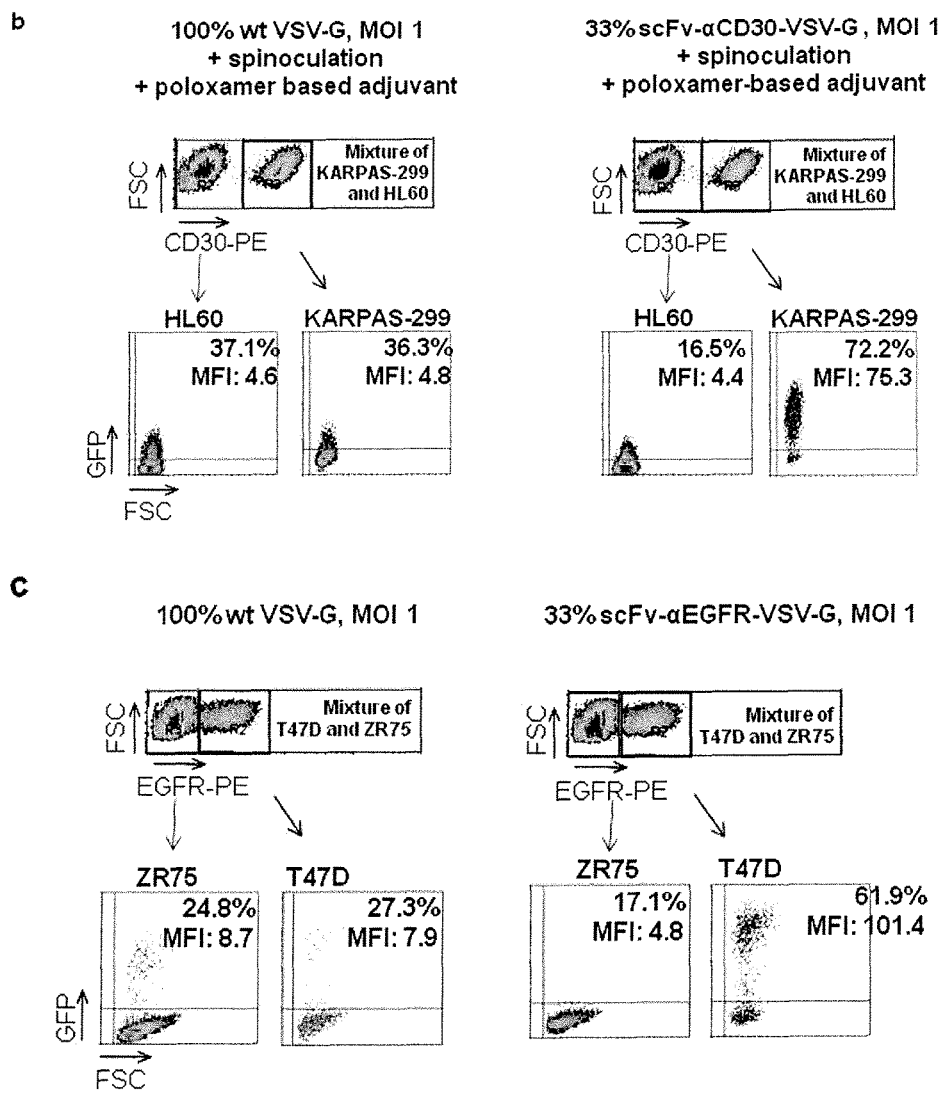

FIG. 5: ScFv-VSV-G-added target cell transduction in the presence of non-target cells in a competitive transduction assay. (a) FACS analysis of CD30 expression on the surface of HL60 leukemia cells. (b) KARPAS-299 and HL60 cells or (c) ZR75 and T47D cells were mixed in equal cell numbers and transduced with (left) wt lentiviral particles and (right) 33% scFv-VSV-G-added lentiviral particles at MOI 1. In cytofluorimetric dot blots (FSC vs. CD30 or EGFR expression) two populations could be distinguished: CD30− HL60 and CD30+ KARPAS-299 cells in (b) or EGFR− ZR75 and EGFR+ T47D cells in (c). In lower dot blots (GFP expression vs. FSC), gated cell populations were analysed for copGFP expression. Graphs represent one experiment of three replicates performed.

The examples illustrate the invention:

EXAMPLE 1: MATERIALS AND METHODS

Cell Lines

Human embryonic kidney HEK293T cells were grown in DMEM medium supplemented with 10% fetal calf serum (FCS, Pan Biotech, Aidenbach, Germany) and 2 mM glutamine. The anaplastic large cell lymphoma cell lines KARPAS-299, SUDHL-1 and SUP-M2, and the promyelocytic leukemia cell line HL60 were cultured in RPMI 1640 medium supplemented with 10% FCS and 2 mM glutamine. The epithelial breast tumour cell lines ZR75 and T47D were grown in RPMI medium with 10% FCS, 2 mM glutamine and 0.2 U/ml bovine insulin (Cell Applications Inc, San Diego, Calif.).

Engineering of scFv-αCD30–/scFv-αEGFR-VSV-G Plasmids

An MfeI restriction site was added via error-prone PCR in the SS of VSV-G (serotype Indiana) available in the packaging vector pMD2.G (available from e.g. Addgene.org). To introduce a His-tag at the N-terminus, scFv-αCD30 and scFv-αEGFR cDNA (these sequences can be ordered from suppliers such as e.g. GeneArt®) was amplified with an MfeI-His-tag sense primer (5'GCGACCAATTGCCATCAT-CATCATCATCATGCCCAGGT CAAGCTGCAGGAGTG-GACTGAACTGGCAAAG; SEQ ID NO: 11) and an antisense primer, including half a linker sequence (flexible linker: GGGSGGGSSGGGS) harbouring an XhoI site (5'GTAATCTCGAGCCACCTCCTGAACCGCCTCCCC-GTTTGATTTCCAGCTTGGTGCCACACCGAACGTG-GCG; SEQ ID NO: 12). When added, the other half of the linker was attached to the N-terminus of VSV-G by PCR (5'GTTATCTCGAGCGGAGGCGGTTCAAAGTTCAC-CATAGTTTTTCCACACAACAAAAGAAACTG (SEQ ID NO: 13) and 5'GTATTACCGGTTCCTGGGTTTTTAG-GAGCAAGATAGCTGAGATCCACTG (SEQ ID NO: 14) using the AgeI restriction site within VSV-G). Both products were double digested with either MfeI/XhoI or XhoI/AgeI, and reinserted into pMD2.G (linearised by MfeI/AgeI digest). FastDigest restriction enzymes were purchase from Fermentas (Vilnius, Lithuania); oligonucleotides were obtained from Eurofins MWG Operon (Ebersberg, Germany).

Lentivirus Production

The lentiviral transduction vector pGreenPuro (System Biosciences, Mountain View, Calif., USA) allows expression of copGFP driven by an internal CMV promoter. Replication-defective lentiviral particles were produced by transient co-transfection of HEK293T cells in 10 cm petri dishes with 8 µg of pGreenPuro, 16 µg and 8 µg of packaging plasmids pMDLg/pRRE and pRSV.Rev (available from e.g. Addgene.org), and 4 µg of varying ratios of pMD2.G, pMD2.G scFv-αCD30 or -αEGFR. For transfection, lipofectamine 2000 (Life Technologies, Carlsbad, Calif., USA) was used according to the manufacturer's instructions. The virus particles were harvested 48 h after transfection, cleared of cell debris by low-speed centrifugation and filtered using 0.45 µm Stericup filters. The lentivirus supernatant was concentrated by ultrafiltration using Amicon-20 columns (Millipore, Billerica, Mass., USA) as previously described [24]. Concentrated lentivirus aliquots were stored at –80° C. Virus titers (virus particles per ml concentrated aliquot) were determined by QuickTiter™ Lentivirus Quantitation p24 ELISA (BioCat, Heidelberg, Germany) according to the company's protocol using serially diluted lentivirus aliquots.

Immunoblotting Assay

For the preparation of virus protein, 2 µl of concentrated lentivirus solution were denatured by incubation for 10 min at 95° C. in urea sample buffer (5% sodium dodecyl sulfate (SDS), 8 M urea, 200 mM Tris-HCl, 0.1 mM EDTA, 0.03% bromphenol blue, 2.5% dithiothreitol, pH 8.0) [25]. The samples were fractionated in SDS polyacrylamide gels (14%) and transferred to nitrocellulose membranes (GE Healthcare, Little Chalfont, UK). His-tagged scFv-αCD30- or scFv-αEGFR-VSV-G were detected using mouse anti-His antibody (clone 13/45/31, Dianova, Hamburg, Germany) followed by a horseradish peroxidase conjugated anti-mouse antibody (Santa Cruz Biotechnology, Santa Cruz, Calif., USA). Lentiviral core protein p24, detected with a mouse antibody (BioCat, Heidelberg, Germany), was used as an internal reference for lentiviral proteins. The blotted membranes were developed with the ECL advance western blot detection system (GE Healthcare) as recommended by the supplier.

Lentiviral Transduction

HEK293T, ZR75 and T47D cells ($2 \times 10^5$ cells per well) were covered with 1 ml medium containing lentivirus with or without 10 µl of poloxamer-based chemical adjuvant (LentiBoost™ Sirion Biotech GmbH, Martinsried, Germany) [23] at different MOI (lentivirus particles per cell). After 24 h incubation at 37° C. and 5% $CO_2$, the supernatant was exchanged to fresh medium and incubated for additional 24 h.

KARPAS 299, SUDHL-1 or SUP-M2 suspension cells ($10^6$ cells per well) were resuspended in 1 ml medium containing lentivirus. Plates were centrifuged at 800 g for 90 min (spinoculation). SUDHL-1 cells were washed and resuspended in fresh medium directly after spinoculation and incubated for 48 h. Following centrifugation, KARPAS-299, SUP-M2 and HL60 cells were incubated overnight in 1 ml medium containing lentivirus, then washed, resuspended in fresh culture medium and incubated for additional 24 h. For competitive assays mixtures of $5 \times 10^5$ KARPAS-299 and $5 \times 10^5$ HL60 cells or $10^5$ T47D and $10^5$ ZR75 cells were resuspended in 1 ml medium containing lentivirus with the poloxamer-based adjuvant LentiBoost. Suspension cells were centrifuged at 800 g for 90 min and incubated overnight, then washed and again incubated for 24 h.

Cytofluorimetric Analysis

Following lentiviral transduction, cells were washed and resuspended in PBS. 30,000 events were analysed for forward and sideward scatter characteristics and for green fluorescence light emission at 530 nm using FACSDiva (BD Biosciences, Heidelberg, Germany). The median fluorescent intensity (MFI) quantifies the shift in fluorescence intensity of transduced cells.

For detection of CD30 or EGFR surface expression, $10^6$ cells were washed twice with PBS supplemented with 2% FCS and incubated in 100 µl antibody dilution (1:20 in PBS+2% FCS; FITC-conjugated αCD30 or αEGFR antibody and isotype control, Dako, Denmark; PE-conjugated αCD30 or αEGFR antibody, BioLegend, San Diego, Calif., USA) for 1 h on ice. Prior to cytometric detection (FITC: 530 nm; PE: 610 nm), cells were washed twice and resuspended in PBS+2% FCS.

Statistical Analysis

All experiments were performed with duplicate technical and triplicate biological replicates. Mean±standard deviation (SD) values are depicted unless stated otherwise. Results obtained were statistically evaluated using t-test with the help of the statistic software SigmaPlot (Systat Software Inc, San Jose, Calif.). Statistical significance was considered at *p<0.05 levels.

EXAMPLE 2: DESIGN AND PRODUCTION OF LENTIVIRAL PARTICLES CONTAINING SCFV-VSV-G FUSIONS

For production of VSV-G pseudotyped lentiviral particles, HEK293T cells were transiently transfected with a four-plasmid mix containing a copGFP expressing lentivirus expression vector and three packaging plasmids—one of them encoding for VSV-G (pMD2.G). To incorporate a single chain antibody fragment recognizing CD30 or EGFR (scFv-αCD30 or -αEGFR) respectively, a novel VSV-G fusion protein was designed, containing an N-terminal His-tag followed by the scFv antibody fragment, and a flexible linker (GGGSGGGSSGGGS) inserted between the signal sequence (SS) and the N-terminus of full length VSV-G (FIG. 1). To determine the optimal lentivirus vector configuration, GFP-encoding scFv-retargeted lentiviral particles were generated with different stoichiometric ratios of pMD2.G plasmids encoding either wild type (wt) or scFv-αEGFR-added VSV-G. Antibody-retargeted particles with 10, 20, 33 and 67% scFv-αEGFR-VSV-G could be produced in comparable yields (quantified in ELISA assays detecting lentiviral core protein p24) (FIG. 2a). High ratios of scFv-αEGFR-VSV-G encoding plasmids in the production mix resulted in lower yields compared to wt VSV-G LV productions. The incorporation of scFv-αEGFR-VSV-G in lentiviral particles was demonstrated by immunoblot of scFv-VSV-G pseudotyped particles. Though possible accumulation of membrane-bound VSV-G was observed (white cloud), a clear band for His-tagged scFv-αEGFR-VSV-G was detectable (FIG. 2b).

EXAMPLE 3: TRANSDUCTION OF EGFR+ HEK293T CELLS WITH DIFFERENT RATIOS OF SCFV-αEGFR-ADDED LENTIVIRAL PARTICLES

GFP-encoding antibody-retargeted particles were tested for their capacity to infect EGFR+ HEK293T cells in cytometric assays (FIG. 2c-e) at MOI 1. While wt VSV-G lentiviral particles could infect 24.1% of HEK293T cells, scFv-VSV-G-added lentiviral particles were able to significantly enhance infection rates up 2.5-fold (62.3% for particles with 33% scFv-αEGFR-VSV-G). Antibody-retargeted lentiviral particles carrying 67% scFv-αEGFR-VSV-G were only half as infectious (13.4%) as wt VSV-G lentiviral particles and homotypic (100%) scFv-αEGFR-VSV-G lentiviral particles were not infectious (FIG. 2d, e).

EXAMPLE 4: FACTORS THAT AFFECT ANTIBODY-RETARGETED LENTIVIRAL TRANSDUCTION

Lentiviral particles displaying scFv-αEGFR-VSV-G were able to infect EGFR+ HEK293T cells. To check for specificity of enhanced transduction rates, both antigen-expressing T47D breast cancer cells and antigen-negative ZR75 cells were used as cellular models (FIG. 3a). In T47D cells 33% scFv-αEGFR-VSV-G lentiviral particles showed best performance, enhancing infection rates 2-fold (67.5%) compared to wt VSV-G lentiviral particles (33.7%). As seen before, virus productions containing higher plasmid amounts of scFv-added VSV-G (100%) failed to infect EGFR+ cells in cytometric assays (FIG. 3b). Transduction of EGFR− ZR75 cells with 33% scFv-αEGFR-VSV-G lentiviral particles did not result in an increased transduction rate (FIG. 3c), proving that the enhancing effect of scFv-targeted lentivirus particles correlates with antigen presence on the target cell surface.

Both, the size of fused protein domains and the attachment mechanism are important for proper folding and function of the recombinant fusion proteins. To evaluate the role of the fusion linker (13 amino acids: GGGS GGGSS GGGS) we designed a scFv-αEGFR-VSV-G without a linker sequence separating the variable light chain sequence of the scFv-αEGFR antibody fragment and the VSV-G gene sequence (cf. FIG. 1a). Producing 33% scFv-αEGFR-VSVG lentiviral particles without a fusion linker led to a strong decrease in virus yields compared to 33% scFv-αEGFR-VSVG lentiviral particle production ($2.5 \times 10^8$ vs. $9.1 \times 10^8$ virus particles per ml). Antibody-retargeted particles without fusion linkers failed to increase transduction rates of T47D cells (FIG. 3d). We conclude that a linker sequence between antibody and VSV-G mediates the improved functionality of scFv-VSV-G retargeted lentivirus particles.

EXAMPLE 5: OPTIMIZED TRANSDUCTION PROTOCOL FOR CD30+ LYMPHOMA CELLS

Low LV infection titers (MOI 2 or less) are sufficient to transduce most adherent epithelial cells. However, in suspension and hematopoietic cells, e.g. lymphoma cells, even high LV titers (MOI 10) transduce only a part of the cell population. Therefore an optimized infection protocol was developed by combining spinoculation, a poloxamer-based chemical adjuvant and scFv-retargeted VSV-G envelopes. KARPAS-299, SUP-M2 and SUDHL-1 lymphoma cells express high CD30 surface levels compared to CD30− HEK293T cells (FIG. 4a). Standard transduction of lymphoma cells at MOI 10 resulted in transduction rates of 20% to 40% (FIG. 4b-d). Adding spinoculation and chemical adjuvants lead to an increase in lentiviral infection. Additionally, modification of 33% of the lentiviral surface with scFv-αCD30-VSV-G pushed transduction rates to levels higher than 90% (4-fold improvement over wt-VSV-G for SUDHL-1 cells) at MOI 10. Even when lentiviral particle titers were reduced to MOI 1, 50% of lymphoma cells could be transduced with this transduction protocol. Compared to the previous state-of-the art protocol, a more than 10-fold increase in efficiency was thus obtained with the optimized system. In contrast, CD30− HEK293T cells could not benefit from the modification of the lentiviral surface, underlining the necessity of specific antigen presence. These data correlate with effects on EGFR− ZR75 cells when scFv-αEGFR-VSV-G added lentivirus was used (FIG. 3c). For all tested cell types, the use lentiviral vectors pseudotyped with 33% scFv-VSV-G yielded the best transduction results.

EXAMPLE 6: SCFV-VSV-G-ADDED TARGET CELL TRANSDUCTION IN THE PRESENCE OF NON-TARGET CELLS

In monotypic culture, scFV-retargeted lentiviral particles were able to transduce lymphoma and epithelial tumour cells more effectively than wt VSV-G pseudotyped vectors. The specificity was further tested in two competitive cell-transduction experiments: First, adherent EGFR+ T47D and EGFR− ZR75 cells were co-cultured (FIG. 5a). Second, CD30+ KARPAS-299 cells were mixed with CD30− HL60 promyelocytic leukemia cells, both cultured in suspension (FIG. 5b,c). Both mixtures were infected with either 100% wt or 33% scFv-αCD30-VSV-G lentiviral particles at MOI 1 under optimized conditions (+ spinoculation, + poloxamer-based adjuvant). Using 100% wt-VSV-G pseudotyped lentiviral particles, each of the cell mixtures showed comparable transduction rates by FACS analysis (24.8% transduced ZR75 and 27.3% transduced T47D cells in the first setting, and 37.1% transduced HL-60 cells and 36.3% transduced KARPAS-299 cells in the second setting). Overall, in experiments using suspension lymphoma and HL60 cells, lower MFI (median fluorescence intensity) values of GFP-expression were measured compared to the transduction of adherent T47D and ZR75 cells.

In both cases, the transduction equilibrium was shifted towards the antigen-positive cell type within a mixture (61.9% of EGFR$^+$ T47D cells versus 17.1% transduced EGFR$^-$ ZR75 cells, and 72.2% CD30$^+$ KARPAS-299 cells versus 16.5% transduced CD30$^-$ HL60 cells, respectively) when scFv-retargeted lentiviral particles were used. These findings demonstrate a gain of relative specificity of antibody-retargeted lentiviral particles towards their target cells even in the presence of competing non-target cells.

EXAMPLE 7: DISCUSSION

A novel type of lentiviral particle has been developed, carrying scFV-retargeted VSV-G glycoproteins displaying linker-fused single chain antibody fragments (scFv) against the lymphoma tumour antigen CD30 or the broad epithelial tumour antigen EGFR. When combined with spinoculation and a poloxamer-based adjuvant, high transduction rates in antigen-positive cells were achieved at low MOI.

Various chemical adjuvants can be used for enhancing lentivirus gene transfer, including cationic polymers or lipid based chemicals that neutralize membrane charges [26-28]. For clinical applications, lentivirus transduction protocols are often based on the use of the retroviral transduction enhancer retronectin, a fibronectin-derived fragment [29]. Retronectin was reported to promote the activity of GALV-pseudotyped and RD114-pseudotyped vectors, but to a lesser extend transduction of VSV-G pseudotyped vectors [22, 30, 31]. Moreover the dosage of retronectin for suspension cells is difficult due to its surface-based activity.

The search for new adjuvants suitable for clinical transduction protocols of lentivirus vectors led to the recent discoveries of the cationic peptide Vectofusin-1 and the amphiphilic Poloxamer Pluronic® F-108 (Poly(ethylene glycol)-block-poly(propylene glycol)-block-poly(ethylene glycol) having an average Molecular weight of ~14,600 (Sigma Aldrich), showing improved gene delivery to CD34$^+$ hematopoetic cells and primary T-cells [32, 23]. For Poloxamer F108, toxicity levels are low even at high concentrations (>5 mg/ml) and there is an FDA drug master file available for the Poloxamer 338 with the identical chemical composition available from BASF (Kolliphor P 338).

In the past, antibody-retargeting studies had been undertaken using retroviruses that display antibodies fused to other glycoproteins or with conjugate-based approaches [33-36]. VSV-G-based studies exploit the advantages of VSV-G as a potent glycoprotein in terms of stabilization of particle assembly and membrane fusion capacity [37], which can be maintained after insertion of new protein domains at the N-terminus of VSV-G [38, 39]. By adding a collagen-binding domain [11], an antigen-binding ZZ-domain [12] or a fibrinogen-binding site [13] to the N-terminus of VSV-G, modified lentiviral particles (some as mixtures with wt VSV-G) could be immobilized to collagen/antibody-coated matrices or fibrin hydrogels. Cells subsequently cultured on the virion-attached matrices were transduced up to 5 times more efficiently. Due to temperature sensitive membrane trafficking of modified VSV-G during particle production in one study [11], acceptable titers could only be achieved at 30° C. These methods demonstrate enhanced immobilization of viral particles and therefore increased spatially-controlled viral uptake when adherent cells were brought in close contact to immobilized virions and polybrene, but do not alter the specificity of the lentiviral particle itself.

To increase the selectivity of lentiviral particles, Kaikkonen et al. [40] fused streptavidin to the transmembrane domain of VSV-G on gp64-pseudotyped envelopes to induce conjugate-based binding of αEGFR- and αCD46-avidin-antibodies. This resulted in 2-fold higher transduction rates in adherent lung, liver and ovarian cancer cell lines at MOI 0.2 to 1.2 in the presence of polybrene. A non-covalent binding approach like this however can have limitations as biotinylated antibody-adaptors are prone to dissociation due to biotinidase activity in serum [41].

Dreja and Piechaczyk [14] added a foreign signal sequence fused to a scFv antibody fragment directed against ubiquitously expressed human MHC-I to the N-terminus of full-length VSV-G (without linker). They showed formation and cellular binding of antibody-retargeted lentiviral particles, but achieved poor titers and low infectivity of human cells. They achieved a 5-fold higher selectivity for human cell transduction (M01 not indicated) compared to VSV-G lentiviral particles carrying a non-binding scFv antibody fragment in the presence of polybrene. Our results support these findings as homotypic (100%) scFv-added VSV-G particles failed to transduce target cells at MOI 1. Antibody fragments might mask the receptor-binding site of VSV-G or spatial interference might lead to inhibited fusion capacity of VSV-G [42, 43].

In the present study, specificity could be increased at high transduction rates by producing lentiviral particles presenting a mixture of wt and scFv-added VSV-G. In all experiments, best results were obtained at a ratio of 33% for scFv-added VSV-G. Combined with spinoculation and a poloxamer-based chemical adjuvant, 4-fold higher transduction of antigen-positive lymphoma cells could be obtained, even in the presence of non-target HL 60 cells.

CONCLUSION

The recombinant scFv-VSV-G fusion strategy as described herein, and in particular the preferred strategy in the above examples, is readily adaptable to different cellular antigens by altering the affinity of the scFv antibody fragment. Significant increase of gene delivery rates in combination with spinoculation and chemical adjuvants in challenging non-adherent cellular models was achieved, which is beneficial for industrial and pharmaceutical lentivirus applications.

FURTHER REFERENCES

1. Bukrinsky M I, Haggerty S, Dempsey M P, Sharova N, Adzhubel A, Spitz L et al. A nuclear localization signal within HIV-1 matrix protein that governs infection of non-dividing cells. Nature 1993; 365:666-669.
2. Gaspar H B, Cooray S, Gilmour K C, Parsley K L, Zhang F, Adams S et al. Hematopoietic stem cell gene therapy for adenosine deaminase-deficient severe combined immunodeficiency leads to long-term immunological recovery and metabolic correction. Sci Transl Med 2011; 3:97ra80.
3. Gaspar H B, Cooray S, Gilmour K C, Parsley K L, Adams S, Howe S J et al. Long-term persistence of a polyclonal T cell repertoire after gene therapy for X-linked severe combined immunodeficiency. Sci Transl Med 2011; 3:97ra79.
4. Lamb L S, Bowersock J, Dasgupta A, Gillespie G Y, Su Y, Johnson A et al. Engineered drug resistant γδ T cells kill glioblastoma cell lines during a chemotherapy challenge: a strategy for combining chemo- and immunotherapy. PLoS One 2013; 8(1):e51805.
5. Chen F, Cai B, Gao Y, Yuan X, Cheng F, Wang T et al. Suicide gene-mediated ablation of tumor-initiating mouse pluripotent stem cells. Biomaterials 2013; 34(6):1701-1711.
6. Finkelshtein D, Werman A, Novick D, Barak S, Rubinstein M. LDL receptor and its family members serve as the cellular receptors for vesicular stomatitis virus. Proc Natl Acad Sci USA 2013; 110(18):7306-7311.
7. Burns J C, Friedmann T, Driever W, Burrascano M, Yee J K. Vesicular stomatitis virus G glycoprotein pseudotyped retroviral vectors: concentration to very high titer and efficient gene transfer into mammalian and nonmammalian cells. Proc Natl Acad Sci USA 1993; 90:8033-8037.
8. Li Y, Drone C, Sat E, Ghosh H P. Mutational analysis of the vesicular stomatitis virus glycoprotein G for membrane fusion domains. J Virol 1993; 67:4070-4077.
9. Strappe P M, Hampton D W, Cachon-Gonzalez B, Fawcett J W, Lever A. Delivery of a lentiviral vector in a Pluronic F127 gel to cells of the central nervous system. Eur J Pharm Biopharm 2005; 61:126-133.
10. Waehler R, Russell S J, Curiel D T. Engineering targeted viral vectors for gene therapy. Nat Rev Genet 2007; 8:573-587.
11. Guibinga G H, Hall F L, Gordon E M, Ruoslahti E, Friedmann T. Ligand-modified vesicular stomatitis virus glycoprotein displays a temperature-sensitive intracellular trafficking and virus assembly phenotype. Mol Ther 2004; 9(1):76-84.
12. Kameyama Y, Kawabe Y, Ito A, Kamihira M. Antibody-dependent gene transduction using gammaretroviral and lentiviral vectors pseudotyped with chimeric vesicular stomatitis virus glycoprotein. J Virol Methods 2008; 153 (1):49-54.
13. Padmashali R M, Andreadis S T. Engineering fibrinogen-binding VSV-G envelope for spatially- and cell-controlled lentivirus delivery through fibrin hydrogels. Biomaterials 2011; 32(12):3330-3339.
14. Dreja H, Piechaczyk M. The effects of N-terminal insertion into VSV-G of an scFv peptide. Virol J 2006; 3:69.
15. Guinivan P, Ladda R L. Decrease in epidermal growth factor receptor levels and production of material enhancing epidermal growth factor binding accompany the temperature-dependent changes from normal to transformed phenotype. Proc Natl Acad Sci USA. 1979; 76(7):3377-3381.
16. Yewale C, Baradia D, Vhora I, Patil S, Misra A. Epidermal growth factor receptor targeting in cancer: a review of trends and strategies. Biomaterials. 2013; 34(34):8690-8707.
17. Udayachander M, Meenakshi A, Ansamma J, Muthiah R. Lymphoma-associated antigen (LAA): isolation, characterization and clinical evaluation. Br J Cancer. 1983; 48(5):717-725.
18. Deutsch Y E, Tadmor T, Podack E R, Rosenblatt J D. CD30: an important new target in hematologic malignancies. Leuk Lymphoma. 2011; 52(9):1641-1654.
19. Matthey B, Borchmann P, Schnell R, Tawadros S, Lange H, Huhn M et al. Metalloproteinase inhibition augments antitumor efficacy of the anti-CD30 immunotoxin Ki-3 (scFv)-ETA' against human lymphomas in vivo. Int J Cancer 2004; 111:568-574.
20. Braschoss S, Hirsch B, Duebel S, Stein H, Duerkop H. New anti-CD30 human pancreatic ribonuclease-based immunotoxin reveals strong and specific cytotoxicity in vivo. Leuk Lymphoma 2007; 48:1179-1186.
21. Pardo A, Stoecker M, Kampmeier F, Melmer G, Fischer R, Thepen T et al. In vivo imaging of immunotoxin treatment using Katushka-transfected A-431 cells in a murine xenograft tumour model. Cancer Immunol Immunother 2012; 61:1617-1626.
22. Ingrao D, Majdoul S, Seye A K, Galy A, Fenard D. Concurrent Measures of Fusion and Transduction Efficiency of Primary CD34+ Cells with Human Immunodeficiency Virus 1-Based Lentiviral Vectors Reveal Different Effects of Transduction Enhancers. Hum Gene Ther Methods 2013; In print.
23. Höfig I, Atkinson M J, Mall S, Krackhardt A M, Thirion C, Anastasov N. Poloxamer synperonic F108 improves cellular transduction with lentiviral vectors. J Gene Med 2012; 14:549-560.
24. Anastasov N, Bonzheim I, Rudelius M, Klier M, Dau T, Angermeier D et al. C/EBPβ expression in ALK-positive anaplastic large cell lymphomas is required for cell proliferation and is induced by the STAT3 signaling pathway. Haematologica 2010; 95(5):760-767.
25. Funke S, Maisner A, Muehlebach M D, Koehl U, Grez M, Cattaneo R et al. Targeted cell entry of lentiviral vectors. Mol Ther 2008; 16:1427-1436.
26. Cornetta K, Anderson W F. Protamine sulfate as an effective alternative to polybrene in retroviral-mediated gene-transfer: implications for human gene therapy. J Virol Methods 1989; 23:187-194.
27. Toyoshima K, Vogt P K. Enhancement and inhibition of avian sarcoma viruses by polycations and polyanions. Virology 1969; 38:414-426.
28. Davis H E, Rosinski M, Morgan J R, Yarmush M L. Charged polymers modulate retrovirus transduction via membrane charge neutralization and virus aggregation. Biophys J 2004; 86:1234-1242.
29. Hanenberg H, Xiao X L, Dilloo D, Hashino K, Kato I, Williams D A. Colocalization of retrovirus and target cells on specific fibronectin fragments increases genetic transduction of mammalian cells. Nat Med 1996; 2:876-882.
30. Sandrin V, Boson B, Salmon P, Gay W, Nègre D, Le Grand R et al. Lentiviral vectors pseudotyped with a modified RD114 envelope glycoprotein show increased stability in sera and augmented transduction of primary lymphocytes and CD34+ cells derived from human and nonhuman primates. Blood 2002; 100:823-832.
31. Haas D L, Case S S, Crooks G M, Kohn D B. Critical factors influencing stable transduction of human CD34(+) cells with HIV-1-derived lentiviral vectors. Mol Ther 2000; 2:71-80.
32. Fenard D, Ingrao D, Seye A, Buisset J, Genries S, Martin S et al. Vectofusin-1, a new viral entry enhancer, strongly promotes lentiviral transduction of human hematopoietic stem cells. Mol Ther Nucleic Acids 2013; 2:e90.
33. Wu D T, Seita Y, Zhang X, Lu C W, Roth M J. Antibody-directed lentiviral gene transduction for live-cell monitoring and selection of human iPS and hES cells. PLoS One 2012; 7:e34778.
34. Zhang K X, Moussavi M, Kim C, Chow E, Chen I S, Fazli L et al. Lentiviruses with trastuzumab bound to their envelopes can target and kill prostate cancer cells. Cancer Gene Ther 2009; 16:820-831.
35. Morizono K, Xie Y, Ringpis G E, Johnson M, Nassanian H, Lee B et al. Lentiviral vector retargeting to P-glycoprotein on metastatic melanoma through intravenous injection. Nat Med 2005; 11:346-352.
36. Ayala-Breton C, Barber G N, Russell S J, Peng K W. Retargeting vesicular stomatitis virus using measles virus envelope glycoproteins. Hum Gene Ther 2012; 23:484-491.
37. Farley D C, lqball S, Smith J C, Miskin J E, Kingsman S M, Mitrophanous K A. Factors that influence VSV-G pseudotyping and transduction efficiency of lentiviral vectors—in vitro and in vivo implications. J Gene Med 2007; 9:345-356.
38. Schlehuber L D, Rose J K. Prediction and identification of a permissive epitope insertion site in the vesicular stomatitis virus glycoprotein. J Virol 2004; 78(10):5079-5087.
39. Yu J H, Schaffer D V. Selection of novel vesicular stomatitis virus glycoprotein variants from a peptide insertion library for enhanced purification of retroviral and lentiviral vectors. J Virol 2006; 80:3285-3292.
40. Kaikkonen M U, Lesch H P, Pikkarainen J, Raety J K, Vuorio T, Huhtala T et al. (Strept)avidin-displaying lentiviruses as versatile tools for targeting and dual imaging of gene delivery. Gene Ther 2009; 16:894-904.
41. Jeong Lee H, Pardridge W M. Drug targeting to the brain using avidin-biotin technology in the mouse. J Drug Target 2000; 8:413-424.
42. Roche S, Albertini A A, Lepault J, Bressanelli S, Gaudin Y. Structures of vesicular stomatitis virus glycoprotein: membrane fusion revisited. Cell Mol Life Sci 2008; 65:1716-1728.
43. Albertini A A, Mérigoux C, Libersou S, Madiona K, Bressanelli S, Roche S et al. Characterization of monomeric intermediates during VSV glycoprotein structural transition. PLoS Pathog 2012; 8(2):e1002556.
44. Millington M, Arndt A, Boyd M, Applegate T, Shen S, 2009 Towards a Clinically Relevant Lentiviral Transduction Protocol for Primary Human CD34+ Hematopoietic Stem/Progenitor Cells. PLoS ONE 4(7): e6461. doi: 10.1371/journal.pone.0006461.
45. Lemberg and Martoglio. Requirements for signal peptide peptidase-catalyzed intramembrane proteolysis. Mol Cell. 2002; 10(4):735-44.
46. Schwartz. Origins and evolution of cotranslational transport to the ER. Adv Exp Med Biol. 2007; 607:52-60.
47. Yeagle "The Membranes of Cells", Academic Press, Amsterdam (1993).
48. Luckey "Membrane Structural Biology: With Biochemical and Biophysical Foundations", Cambridge University Press, Cambridge (2008).
49. Yoneda J, Saiki I, Igarashi Y, Kobayashi H, Fujii H, Ishizaki Y, Kimizuka F, Kato I, Azuma I. Role of the heparin-binding domain of chimeric peptides derived from fibronectin in cell spreading and motility. Exp Cell Res. 1995 March; 217(1):169-79.
50. Michalsky, E., Goede, A. and Preissner, R. (2003) Loops In Proteins (LIP)—a comprehensive loop database for homology modelling. Protein Eng. 16, 979-985.
51. Novella. Contributions of vesicular stomatitis virus to the understanding of RNA virus evolution. Curr Opin Microbiol. 2003; 6(4):399-405.
52. Lichty, Power, Stojdl and Bell. Vesicular stomatitis virus: re-inventing the bullet. Trends Mol Med. 2004; 10(5):210-6.
53. Regan and Whittaker. Entry of rhabdoviruses into animal cells. Adv Exp Med Biol. 2013; 790:167-77.
54. Martinez and Wertz. Biological differences between vesicular stomatitis virus Indiana and New Jersey serotype glycoproteins: identification of amino acid residues modulating pH-dependent infectivity. J Virol. 2005; 79(6):3578-85.
55. Fredericksen and Whitt. Vesicular stomatitis virus glycoprotein mutations that affect membrane fusion activity and abolish virus infectivity. J. Virol. 1995; 69:1435-43.
56. Schlehuber and Rose. Prediction and identification of a permissive epitope insertion site in the vesicular stomatitis virus glycoprotein. J Virol. 2004; 78(10):5079-87.].
57. Yee J K, Friedmann T, Burns J C. Generation of high-titer pseudotyped retroviral vectors with very broad host range. Methods Cell Biol. 1994; 43 Pt A:99-112.
58. Cronin J, Zhang X Y, Reiser J. Altering the tropism of lentiviral vectors through pseudotyping. Curr Gene Ther. 2005 August; 5(4):387-98.
59. Bartosch B, Cosset F L. Strategies for retargeted gene delivery using vectors derived from lentiviruses. Curr Gene Ther. 2004 December; 4(4):427-43.
60. Froelich S, Tai A, Wang P. Lentiviral vectors for immune cells targeting. Immunopharmacol Immunotoxicol. 2010 June; 32(2):208-18.
61. Naldini, L. (1998) Lentiviruses as Gene Transfer Agents for Delivery to Non-dividing Cells. Curr. Opin. Biotechnol. 9, 457-463.
62. Robison C. L. and Whitt, M. A.: The Membrane-Proximal Stem Region of Vesicular Stomatitis Virus G Protein Confers Efficient Virus Assembly. Journal of Virology, March 2000, p. 2239-2246.
63. Klimka et al. An anti-CD30 single-chain Fv selected by phage display and fused to *Pseudomonas* exotoxin A (Ki-4(scFv)-ETA') is a potent immunotoxin against a Hodgkin-derived cell line. Br J Cancer. 1999 June; 80(8): 1214-22.
64. Kettleborough C A, Ansell K H, Allen R W, Rosell-Vives E, Güssow D H, Bendig M M. Isolation of tumor cell-specific single-chain Fv from immunized mice using phage-antibody libraries and the re-construction of whole antibodies from these antibody fragments. Eur J Immunol. 1994 April; 24(4):952-8.

The invention claimed is:

1. A nucleic acid molecule comprising or consisting of a nucleic acid sequence encoding
   (a) a vesicular stomatitis virus envelope glycoprotein (VSV-G) linked to a (poly)peptide comprising or consisting of a cell membrane-binding domain, said nucleic acid sequence comprising in 5' to 3' direction
      (i) a first sequence segment encoding an endoplasmic reticulum (ER) signal sequence;
      (ii) a second sequence segment encoding said (poly)peptide comprising or consisting of a cell membrane-binding domain;
      (iii) a third sequence segment encoding a linker; and
      (iv) a fourth sequence segment encoding said VSV-G; and
   (b) a VSV-G not linked to a (poly)peptide comprising or consisting of a cell membrane-binding domain.

2. The nucleic acid molecule of claim 1, wherein said (poly)peptide comprising or consisting of a cell membrane binding-domain encoded by said second sequence segment is selected from the group consisting of a single chain antibody, a single domain antibody, a $V_HH$ antibody fragment, a VNAR single chain antibody and an protein scaffold.

3. The nucleic acid molecule of claim 1, wherein the (poly)peptide comprising or consisting of a cell membrane-binding domain binds specifically to one or more cell membrane constituents selected from the group consisting of glycolipids, phospholipids, oligosaccharides, G-protein-coupled cellular receptors (GPCRs), cluster of differentiation (CD) cell surface proteins, cell surface receptors, cell surface co-receptors and proteins.

4. The nucleic acid molecule of claim 1, wherein
   (a) said first sequence segment encoding said ER signal sequence comprises or consists of the nucleic acid sequence as shown in SEQ ID NO:1;
   (b) said third sequence segment encoding a linker comprises or consists of the nucleic acid sequence as shown in SEQ ID NO:3; and/or
   (c) said fourth sequence segment encoding said VSV-G comprises or consists of the nucleic acid sequence as shown in SEQ ID NO:5.

5. A vector comprising the nucleic acid molecule according to claim 1.

6. A host cell comprising the nucleic acid molecule according to claim 1.

7. A lentiviral vector particle pseudotyped with
   (a) a VSV-G linked to a (poly)peptide comprising or consisting of a cell membrane-binding domain encoded by a nucleic acid molecule comprising or consisting of a cell membrane-binding domain, said nucleic acid molecule comprising in 5' to 3'direction
      (i) a first sequence segment encoding an endoplasmic reticulum (ER) signal sequence;
      (ii) a second sequence segment encoding said (poly)peptide comprising or consisting of a cell membrane-binding domain;
      (iii) a third sequence segment encoding a linker; and
      (iv) a fourth sequence segment encoding said VSV-G; and
   (b) a VSV-G not linked to a (poly)peptide comprising or consisting of a cell membrane-binding domain.

8. A method of producing the pseudotyped lentiviral vector particle of claim 7, the method comprising transfecting into a host cell
   (i) one or more packaging plasmids encoding the lentiviral proteins;
   (ii) a vector comprising the nucleic acid molecule as defined in claim 7; and
   (iii) a vector comprising a nucleic acid molecule encoding a VSV-G not linked to a (poly)peptide comprising or consisting of a cell membrane-binding domain.

9. A method for transducing cells, the method comprising the step of:
   contacting cells to be transduced with the pseudotyped lentiviral vector particle of claim 7 under conditions suitable for transduction,
   thereby transducing said cells.

10. The method of claim 9, further comprising contacting the cells with an adjuvant.

11. The method of claim 10, further comprising a step of spinoculating the pseudotyped lentiviral vector particle with the cells prior to, concomitant with or after contacting said cells with said adjuvant.

12. The method of claim 9, wherein the cells to be transduced are selected from the group consisting of tumour cells, lymphoid lineage cells, epithelial cells, neuronal cells and stem cells or wherein the cells to be transduced are part of a heterogeneous cell population.

13. A kit comprising:
   a nucleic acid molecule as defined in claim 7 and a nucleic acid molecule comprising or consisting of a nucleic acid sequence encoding a VSV-G not linked to a (poly)peptide comprising or consisting of a cell membrane-binding domain;
   and, optionally, instructions for use.

14. A host cell comprising the vector according to claim 5.

15. A method of producing a polypeptide encoded by the nucleic acid molecule of claim 1, the method comprising culturing a host cell comprising the nucleic acid molecule of claim 1 and isolating the produced polypeptide.

16. A kit comprising:
   a polypeptide as defined in item (a) of claim 7 and a VSV-G not linked to a (poly)peptide comprising or consisting of a cell membrane-binding domain;
   and, optionally, instructions for use.

17. A kit comprising:
a pseudotyped lentiviral vector particle according to claim 7;
and, optionally, instructions for use.

18. The method of claim 10, where the adjuvant is a poloxamer having a molecular weight of 12.8 kDa to about 15 kDa.

\* \* \* \* \*